(12) United States Patent
Fahl et al.

(10) Patent No.: US 7,531,562 B2
(45) Date of Patent: May 12, 2009

(54) COMPOSITIONS AND METHODS FOR PROTECTING CELLS DURING CANCER CHEMOTHERAPY AND RADIOTHERAPY

(75) Inventors: William E. Fahl, Madison, WI (US); Nalini Raghavachari, Madison, WI (US); Ming Zhu, Madison, WI (US); John A. Kink, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 473 days.

(21) Appl. No.: 10/881,028

(22) Filed: Jun. 30, 2004

(65) Prior Publication Data

US 2005/0043224 A1 Feb. 24, 2005

Related U.S. Application Data

(62) Division of application No. 09/565,714, filed on May 5, 2000, now abandoned.

(51) Int. Cl.
*A61K 31/425* (2006.01)
(52) U.S. Cl. ...................................... 514/365
(58) Field of Classification Search .................. None
See application file for complete search history.

(56) References Cited

U.S. PATENT DOCUMENTS

| 4,110,450 A | 8/1978 | Barreau et al. ............... 424/250 |
| 4,283,487 A | 8/1981 | Lea et al. ..................... 430/522 |
| 4,816,247 A | 3/1989 | Desai et al. ................... 424/80 |
| 5,753,263 A | 5/1998 | Lishko et al. ............... 424/450 |

OTHER PUBLICATIONS

Sredni et al., Int. J. Cnacer, Jan. 3, 1996;65(1):97-103.*
Aphramaian, M., et al., "Transmucosal passage of poly alkylcyanoacrylate nanocapsules as a new drug carrier in the small intestine," *Biol. Cell*, 1987, 61, 69-76.
Benson, A.M., et al., "Elevation of hepatic glutathione S-transferase activities and protection against mutagenic metabolities of benzo(a) pyrene by dietary antioxidants," *Cancer Res.*, 1978, 38, 4486-4495.
Benson, A.M., et al., "Increase of NAD(P)H: quinine reductase by dietary antioxidants: possible role in protection against carcinogenesis and toxicity," *Proc. Natl. Acad. Sci. USA*, 1980, 77(9), 5216-5220.
Bunting, K., et al., "De Novo expression of transfected human class 1 aldehyde dehydrogenase (ALDH) causes resistance to oxazaposphorine anti-cancer alkylating agents in hamster V79 cell lines," *J. Biol. Chem.*, 1996, 271(20), 11884-11890.

Chung, F.-L., et al., "Effects of butylated hydroxyanisole on the tumorigenicity and metabolism of N-nitrosodimethylamine and N-nitrosopyrrolidine in A/J mice," *Cancer Res.*, 1986, 46, 165-168.
Clapper, M.L., "Chemopreventive activity of oltipraz," *Pharmacol. Therapeutics*, 1998, 78(1), 17-27.
DeLong, M., et al., "Tissue-specific induction patterns of cancer-protective enzymes in mice by tert-Butyl-4-hydroxyanisole and related substituted phenols," *Cancer Res.*, 1985, 45, 546-551.
Desai, M.P., et al., "The mechanism of uptake of biodegradable microparticles in Caco-2 cells is size dependent," *Pharm. Res.*, 1997, 14, 1568-1573.
Dzeletovic, N., et al., "Regulation of dioxin receptor function by omeprazole," *Am. Soc. For Biochem. & Molecular Biol.*, 1997, 12705-12713.
Fahey, J.W., et al., "Antioxidant functions of sulforaphane: a potent inducer of phase II detoxication enzymes," *Food & Chem. Toxicol.*, 1999, 37, 973-979.
Gilbert, S., Developmental Biology, downloaded from www.url.ncbi.nim.nih.gov, on Dec. 22, 2003.
Gray, W.M., et al., "Effect of butylated hydroxyanisole, α-angelica lactone, and β-naphthoflavone on benzo (α) pyrene: DNA adduct formation in vivo in the forestomach, lung, and liver of mice," *Cancer Res.*, 1982, 42, 1199-1204.
Hayes, J., et al., "Cellular response to cancer chemopreventive agents: contribution of the antioxidant responsive element to the adaptive response to oxidative and chemical stress," *Biochem. Soc. Symp.*, 2000, 64, 141-168.
Hecht, Symposium on Phytochemical: Biochemistry and Physiology, 1999, 768S-774S.
Henderson, C.J., et al., "Increased skin tumorigenesis in mice lacking pi class glutathione S-transferases," *Proc. Natl. Acad. Sci. USA*, 1998, 95, 5275-5280.
Hillery, A.M., et al., "Comparative, quanititative study of lymphoid uptake of 60 nm polystyrene particles," *J. Drug Targeting*, 1994, 2, 151-156.
Ho, D., et al., "Quantitative significance of glutathione and glutathione-S-transferase in regulating benzo[a]pyrene anti dio-epoxide level in reconstituted C3H/10T1/2 cell lysates, and comparison to rat liver," *Carcinogenesis*, 1984, 5(2), 143-148.

(Continued)

*Primary Examiner*—Misook Yu
(74) *Attorney, Agent, or Firm*—Quarles & Brady LLP

(57) ABSTRACT

Compositions, pharmaceutical preparations and methods are disclosed for protecting non-neoplastic cells from damage caused by cancer chemotherapeutic agents or radiation therapy, during the course of cancer therapy or bone marrow transplant. These are based on the use of chemoprotective inducing agents that induce or increase production of cellular detoxification enzymes in target cell populations. The compositions and methods are useful to reduce or prevent hair loss, gastrointestinal distress and lesions of the skin and oral mucosa that commonly occur in patients undergoing cancer therapy. Also disclosed is a novel assay system for identifying new chemoprotective inducing agents.

1 Claim, 15 Drawing Sheets

OTHER PUBLICATIONS

Ho, D., et al., "Modification of glutathione levels in C3H/10T1/2 cells and its relationship to benzo (a)pyrene anti-7,8-dihydrodiol 9,10-epoxide-induced cytotoxicity," *J. Biol. Chem.*, 1984, 259(18), 11231-11235.

Ioannou, Y.M., et al., "Characterization of Nedd8, a developmentally down-regulated ubiquitin-like protein," *J. of Biol. Chem.*, 1997, 272, 28557-28562.

Jellinck, P., et al., "Ah receptor binding properties of indole carbinols and induction of hepatic estradiol hydroxylation," *Biochem. Pharmacol.*, 1993, 45(5), 1129-1136.

Jiao, D., et al., "Structure-activity relationships of isothiocyanates as mechanism-based inhibitors of 4-(methylnitrosamino)-1-(3-pyridyl)-1-butanone-induced lung tumorigenesis in A/J mice," *Cancer Res.*, 1994, 15(54), 4327-4333 (abstract only).

Jimenez, J., et al., Treatment with ImuVert/*N*-acetylcysteine protects rats from cycloposphamide/cytarabine-induced alopecia, *Cancer Investigation*, 1992, 10(4), 271-276.

Kelly, et al., *Cancer Res.*, 2000, 60, 957-969.

Kensler, T., et al., "Modulation of aflatoxin metabolism, aflatoxin-*N*-guanine formation, and hepatic tumorigenesis in rats fed ethoxyquin: role of induction of glutathione S-transferases," *Nature*, 1986, 46, 3924-3931.

Kim, S.G., et al., "In vivo radioprotective effects of oltipraz in γ-irradiated mice," *Biochemical Pharmacology*, 1998, 55, 1585-1590.

Lieb, et al., *J. of Investigative Dermatology*, 1992, 99(1), 108-113.

Morse, M.A., et al., "Effects of aromatic isothiocyanates on tumorigenicity, 06-methylguanine formation, and metabolism of the tobacco-specific nitrosamine 4-(methylnitrosamino)-1-(3-pyridyl)-1-butanone in A/J mouse lung," *Cancer Res.*, 1989, 49, 2894-2897 (abstract only).

Niemiec, et al., *Pharmaceutical Res.*, 1995, 12(8), 1184-1188.

Niemiec, S.M., et al., "Perifollicular transgenic expression of human interleukin-1 receptor antagonist protein following topical application of novel liposome-plasmid DNA formulations in vivo," *J. of Pharmac. Sci.*, 1997, 86(6), 701-708.

Sreerama, L., et al., "Human-breast adenocarcinoma MCF-7/0 cells electroporated with cytosolic class 3 aldehyde dehydrogenases obtained from tumor cells and a normal tissue exhibit differential sensitivity to mafosfamide," *Am. Soc. For Pharma. & Experi. Therap.*, 1995, 23(10), 1080-1084.

Tanner, B., et al., "Glutathione, glutathione S-transferase α and II, and aldehyde dehydrogenase content in relationship to drug resistance in ovarian cancer," *Gyn. Oncol.*, 1997, 64, 54-62.

Wasserman, W.W., et al., "Functional antioxidant responsive elements," *Proc. Natl. Acad. Sci. USA*, 1997, 94, 5361-5366.

Wattenberg, L.W., et al., "Inhibitory effects of phenolic compounds on benzo (a) pyrene-induced neoplasia," *Cancer Res.*, 1980, 40, 2820-2823.

Xia, C., et al., "The organization of human GSTP1-1 gene promoter and its response to retinoic acid and cellular redox status," *Biochem. J.*, 1996, 313, 155-162.

Zhang, Y., et al., "Anticarcinogenic activities of sulforaphane and structurally related synthetic norbornyl isothiocyanates," *Proc. Natl. Acad. Sci. USA*, 1994, 91, 3147-3150.

Ioannou, Y.M., et al., "Effect of butylated hydroxyanisole, α-angelica lactone, and β-naphthoflavone on benzo(α)pyrene: DNA adduct formation in vivo in the forestomach, lung, and liver of mice," *Cancer Res.*, 1982, 42, 1199-1204.

* cited by examiner

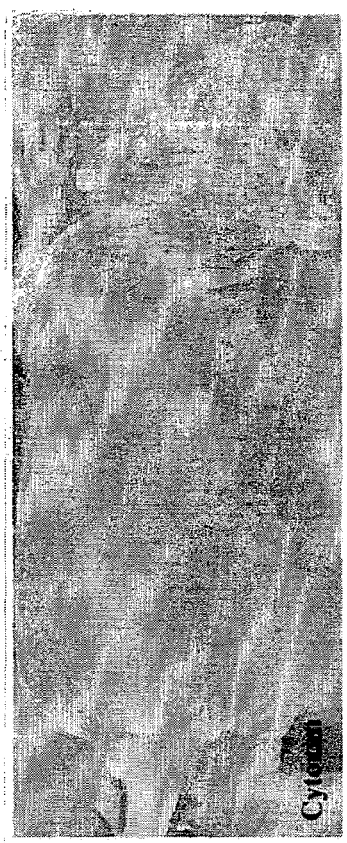
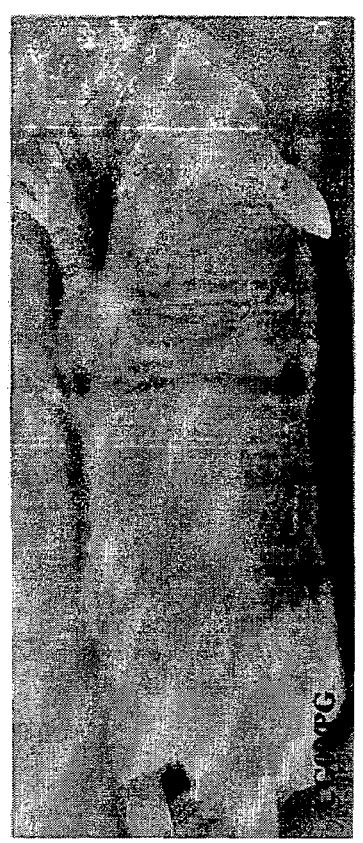
FIG. 2

FIG. 3
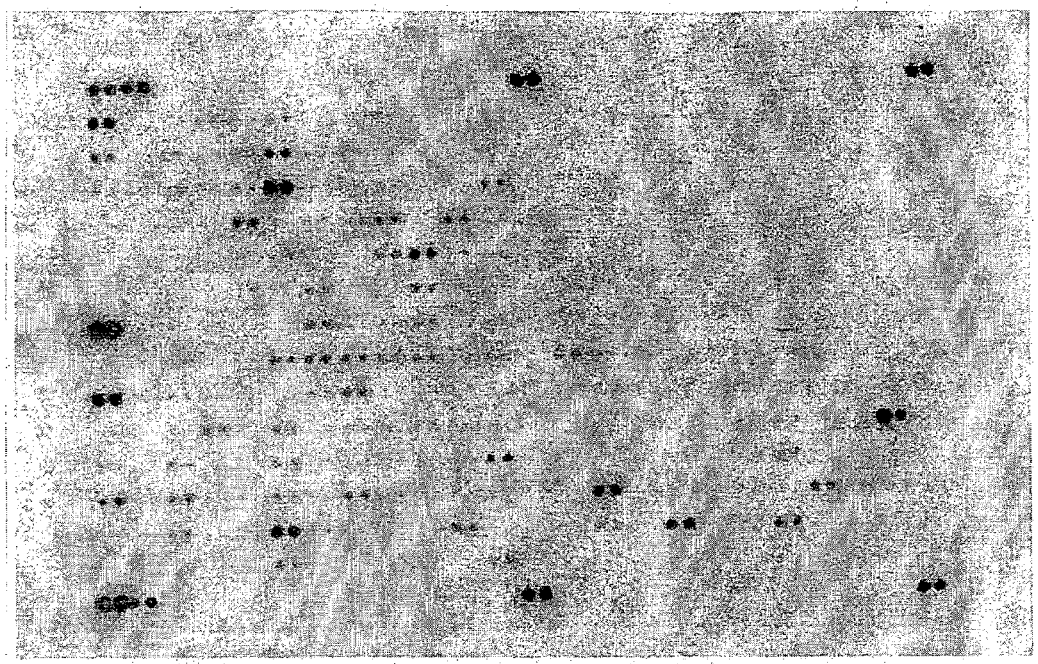
control
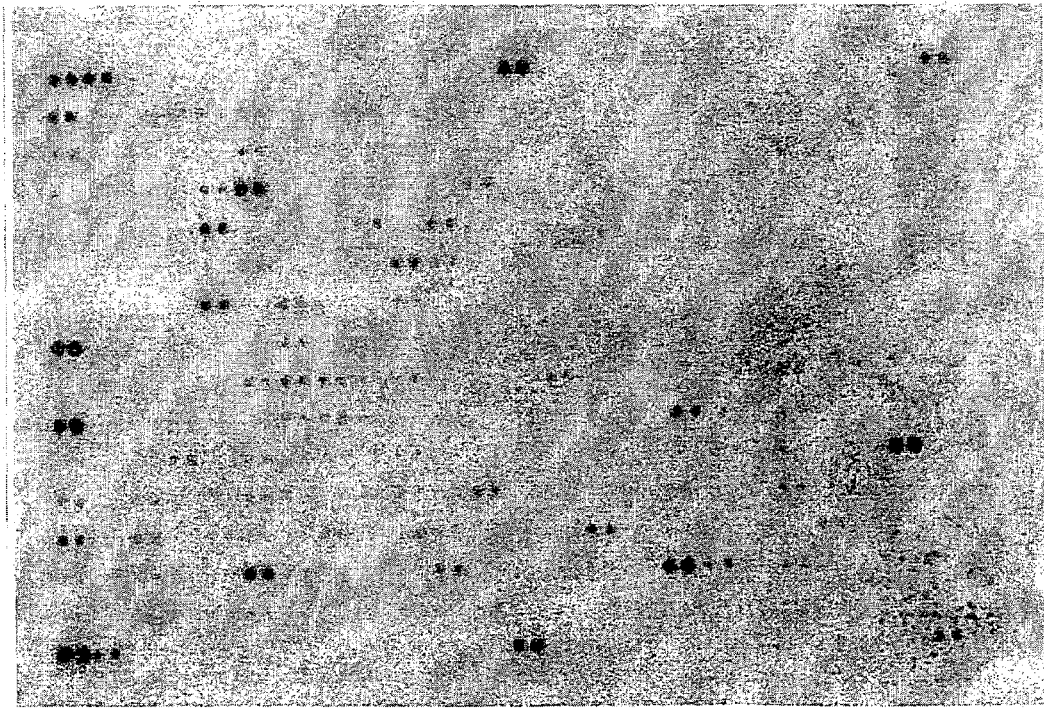
BNF

COMPOSITIONS AND METHODS FOR PROTECTING CELLS DURING CANCER CHEMOTHERAPY AND RADIOTHERAPY

This is a divisional of U.S. application Ser. No. 09/565,714, filed May 5, 2000 now abandoned, the entire contents of which are incorporated by reference herein.

Pursuant to 35 U.S.C. §202(c), it is acknowledged that the U.S. Government has certain rights in the invention described herein, which was made in part with funds from the National Institutes of Health, Grant No. CA22484.

FIELD OF THE INVENTION

The present invention relates to the field of cancer therapy. In particular, the invention provides novel compositions and methods for protecting non-neoplastic cells from the toxic effects of radiotherapy and cancer chemotherapeutic agents.

BACKGROUND OF THE INVENTION

Several publications are referenced in this application in order to more fully describe the state of the art to which this invention pertains. The disclosure of each of these publications is incorporated by reference herein.

Over the past several decades, chemotherapy and radiation therapy coupled with surgery have contributed to a significant reduction in cancer mortality. However, the potential utility of chemotherapeutic drugs in the treatment of cancer has not been fully exploited due to adverse effects associated with the nonspecific cytotoxicity of these agents. Alkylating agents, used alone or in combination with other chemotherapeutic agents, are used in approximately half of all chemotherapy treatments. Alkylating agents interfere with the proliferation of cancerous cells by inhibiting DNA replication. Non-alkylating cancer chemotherapy drugs are also toxic to mammalian cells; they can inhibit multiple sites within a replicating cell, such as (1) synthesis of nucleotides required for DNA replication and (2) microtubule function required for mitosis, to name just two. Radiation therapy, which achieves most of its cell killing properties by generating oxygen radicals within cells, can also efficiently kill mammalian cells. Because the toxic effects of these three commonly used agents are generally not specific to cancer cells, they also affect the growth of normal cells, particularly mitotically active normal cells. As a result, persons being treated with one or more of these cancer therapies commonly develop numerous clinical complications.

Many populations of epithelial cells have a high turnover rate. The toxicity of cancer therapy for epithelial cells accounts for many of the side effects commonly suffered by persons undergoing a regimen of chemotherapy or radiotherapy. These include gastrointestinal distress, nausea, vomiting, diarrhea, loss of appetite, hair loss, bone marrow suppression and skin rash or ulceration at the site of irradiation. These complications can be so difficult to endure that it is not uncommon for people to forego or discontinue recommended cancer therapy treatments in order to avoid the problems. The gastrointestinal disturbances may compromise a patient's chances of recovery, because they make it difficult for him to obtain the nourishment necessary to optimize his ability to fight disease.

Typically, during the course of chemotherapy, the chemotherapeutic agent is administered in sub-optimal doses in order to minimize toxicity and to protect normal, drug-sensitive cells. Reducing the sensitivity of normal cells to chemotherapeutic agents would allow the administration of higher drug dosages and chemotherapy could be rendered more effective.

The successful implementation of protective therapies that promote routine growth and proliferation of normal cells in the presence of radiotherapy or chemotherapeutic agents will allow the use of higher dose aggressive chemotherapy. Two important targets for development of such therapies are (1) the epithelial cells lining the entire gastrointestinal (GI) tract, including the oral mucosa, and (2) the epithelial cells of the skin, including hair follicles and the epidermis.

It appears that chemo- and radiotherapy-associated death and sloughing of GI lumenal cells results in a release of GI damage-associated molecules into the vasculature. These blood-borne molecules, when detected by sites within the brain, trigger the nausea response that is so common among patients receiving chemotherapy. Present treatments with drugs, such as Ondansetron, serve to suppress these brain centers and thus diminish the nausea response. However, the primary destruction of the GI lining still limits the most effective use of chemotherapy. A better mechanism to diminish nausea in these patients is to eliminate the primary destruction of the GI surface and thus prevent the release of damage-associated, nausea-inducing molecules, rather than just suppressing the effects of these molecules in the brain.

New gastrointestinal therapies are being developed that have afforded some protection to normal cells and have maintained the integrity and function of the tissues made up of these cells. Current approaches to protecting normal cells and stimulating proliferation of normal cells involve nutrient stimulation and maximizing the intake of growth factors. Such strategies have been shown to reduce the severity of toxicity and/or shorten the course of drug treatment. However, in spite of these improvements, serious side effects still persist and more effective therapies are needed.

Investigations have also been made into treatment of chemotherapy-induced alopecia. Alopecia or hair loss is the most common hair growth disorder in humans and is often the cause of great concern in affected individuals. In patients with acquired alopecia associated with cancer chemotherapy or radiation therapy, the loss of hair ranked above vomiting as an important concern. Although this condition is generally reversible and regeneration of hair growth occurs within 1-2 months after discontinuation of treatment, hair loss represents a psychologically distressing effect that can cause negative changes in body image, decreased social activity and altered interpersonal relationships and may lead to refusal of further chemotherapy.

The phenomenon of chemotherapy-induced alopecia is believed to result from cytotoxic and apoptosis related damage to the hair follicle. Several studies have shown evidence that the pathobiologic mechanisms that underlie chemotherapy induced follicle damage are characterized by bulging of the dermal papilla, kinking and distension of the follicular canal and disruption of the melanogenic apparatus.

A variety of approaches have been employed in an attempt to protect patients from chemotherapy-induced alopecia. These have included physical modules that temporarily decrease scalp blood flow and drug contact time with the hair follicle, but the patient tolerance was very poor. These poor results led to the development of scalp cooling methods that decrease both the metabolic rate of follicular stem cells and blood flow to the follicle matrix but this strategy was found to be unsuccessful. The use of dietary α-tocopherol a free radical scavenger, was shown to have a protective effect in rabbits but not in humans. Minoxidil 2% solution was also found to be ineffective in treating chemotherapy induced alopecia.

Pre-treatment of rodents with growth factors and cytokines provided some degree of protection against alopecia induced by ARA-C (cytosine arabinoside) but not the commonly used cancer drug cytoxan.

Reversal of cyclophosphamide-or cyclophosphamide/cytarabine-induced alopecia by N-acetylcysteine (NAC) or NAC/ImmuVert, administered parenterally or applied topically in liposomes, has been reported in a rat model system (Jimenez et al., Cancer Investigation 10: 271-276, 1992). NAC is a precursor of glutathione and, as such, is believed to function as a detoxifying agent by increasing intracellular GSH levels. This sort of therapy is limited in efficacy, inasmuch as it has been shown that intracellular GSH levels can only roughly double in a cell by adding exogenous NAC. (See Ho & Fahl, J. Biol. Chem. 259: 11231-11235, 1984; Carcinogenesis 5: 143-148, 1984).

U.S. Pat. No. 5,753,263 to Lishko et al. discloses methods and compositions for treating alopecia induced by certain chemotherapeutic agents, which comprise topical application of an effective amount of a p-glycoprotein, or MDR gene encoding such a protein, in a liposome carrier. This therapy is limited to the particular chemotherapeutic agents that can be exported from a cell via the p-glycoprotein pump. Notably excluded from this list are alkylating chemotherapeutic agents.

Thus, while treatments of the types outlined above may provide some relief from chemotherapy-induced hair loss, their utility is limited, and additional effective therapies are needed.

SUMMARY OF THE INVENTION

In accordance with the present invention, a novel and effective strategy has been devised for protecting rapidly dividing normal cells from damage during the course of radiation therapy or chemotherapy to treat a cancer. This strategy is based on stimulating the natural detoxification systems present in the cells such that they are activated when radiation or chemotherapy is applied, and can thereby protect the cells from damage.

According to one aspect of the invention, a composition for protecting non-neoplastic cells from damage during cancer chemotherapy or radiotherapy is provided. The composition comprises one or more chemoprotective inducing agents, as defined hereinbelow, and a delivery vehicle for delivering the agents to a target population of the non-neoplastic cells. In one preferred embodiment, the target cell population comprises epithelial cells lining hair follicles or comprising the skin epidermis. In another preferred embodiment, the target cell population comprises epithelial cells of the oral mucosa and gastrointestinal lumen.

According to another aspect of the invention, a method is provided for protecting non-neoplastic cells from damage during cancer chemotherapy or radiotherapy. The method comprises administering to a population of epithelial cells a composition as described above, for a time and in an amount effective to protect the non-neoplastic cells from damage during the cancer chemotherapy or radiotherapy. In a preferred embodiment, the method is used to prevent baldness during cancer therapy, by applying the composition to the scalp. In another preferred embodiment, the method is used to prevent gastrointestinal distress due to cancer therapy, by administering the composition orally. In yet another preferred embodiment, the method is used to prevent skin rash and ulceration at the site of irradiation by applying the composition to the skin.

In preferred embodiments of the foregoing aspects of the invention, the chemotherapeutic agent is one or a combination of agents selected from the group consisting of alkylating agents, antimetabolite inhibitors of DNA synthesis, antitumor antibiotics, mitotic spindle poisons and vinca alkaloids. Examples include, but are not limited to, altretamine, asparaginase, bleomycin, busulfan, carboplatin, cisplatin, carmustine, chlorambucil, cladribine, cyclophosphamide, cytarabine, dacarbazine, dactinomycin, daunorubicin, doxorubicin, etoposide, floxuridine, fludarabine phosphate, fluorouracil, hydroxyurea, idarubicin, ifosfamide, lomustine, mechlorethamine, nitrogen mustard, melphalan, mercaptopurine, methotrexate, mitomycin, mitoxantrone, paclitaxel, pentostatin, pliamycin, procarbazine, streptozocin, teniposide, thioguanine, thiotepa, vinblastine and vincristine. The radiation therapy is selected from the group consisting of x-rays, γ-rays, electron beams, photons, α-particles and neutrons.

In a preferred embodiment, the chemoprotective inducing agent is one that induces phase I and phase II drug metabolizing enzymes. Such agents are known in the art (e.g., Hayes et al., Biochem. Soc. Symp. 64, 141-168, 2000) and include such classes of compounds as coumarins, lactones, diterpenes, dithiolethione flavones, indoles, isothiocyanates, organosulfides and phenols. Specific examples include, but are not limited to, 3-tert-butyl-4-hydroxyanisole, 2-tert-butyl-4-hydroxyanisole, 2-tert-butyl-1,4-dimethoxybenzene, 2-tert-butylhydroquinone, 4-hydroxyanisole, ethoxyquin, α-angelica lactone, β-napthoflavone (β-NF), p-methoxyphenol, oltipraz, indole-3-carbinol, omeprazol, coumarin, cafestol, kahweol, quercitin, indole-3-acetonitrile, allyl isothiocyanate, benzyl isothiocyanate, eugenol, phenethyl isothiocyanate, sulphoraphane, allyl methyl disulfide, diallyl sulfide, butylated hydroxytoluene, ellagic acid and ferulic acid.

According to another aspect of the invention, an assay is provided for identifying chemoprotective inducing agents, as defined hereinbelow. The assay comprises the steps of: (a) providing a cell transformed with a DNA construct comprising a reporter gene operably linked to a promoter and to one or more EpRE regulatory elements, (b) exposing the cell to a test compound being screened for possible utility as a chemoprotective inducing agent, and (c) measuring expression of the reporter gene, an increase in the expression in the presence of the test compound, as compared with the expression in the absence of the test compound, being indicative that the test compound is a chemoprotective inducing agent. A kit is also provided in accordance with this aspect of the invention, to facilitate performance of the assay.

According to another aspect of the invention, a method is provided for preventing cancer caused by exposure of cells to environmental carcinogens. This method comprises providing as part of a regular dietary regime one or more chemoprotective inducing agents in an amount effective to stimulate expression of cellular detoxifying enzymes, thereby protecting cells from the effects of the environmental carcinogens, upon exposure thereto.

Other features and advantages of the present invention will be understood from the drawings, detailed description and examples that follow.

BRIEF DESCRIPTION OF THE DRAWINGS

FIG. 2. Effect of chemoprotective inducing agents on hair loss in rat pups treated with cytoxan. Chemoprotective agents were prepared for delivery in a propylene glycol:ethanol: water mixture of a type used for delivery of Minoxidil (Example 1). Results demonstrate that minoxidil carrier was not effective in delivery of chemoprotective inducers. Rat pups treated with CG09 or BNF in the minoxidil carrier suffered hair loss equivalent to that observed in cytoxan-treated animals not pre-treated with the chemoprotective inducer.

FIG. 3. Gene expression pattern of stress genes in rat pups treated with BNF and cytoxan. Rat pups were treated with either carrier alone (control), cytoxan, or BNF and at different time intervals skin samples were collected and cDNA samples prepared from MRNA extracted from the samples. The radiolabeled cDNA synthesized was used to probe a rat stress gene cDNA expression array consisting of 207 stress-related genes (Clontech) according to the manufacturer's protocol.

DETAILED DESCRIPTION OF THE INVENTION

Figure 1:
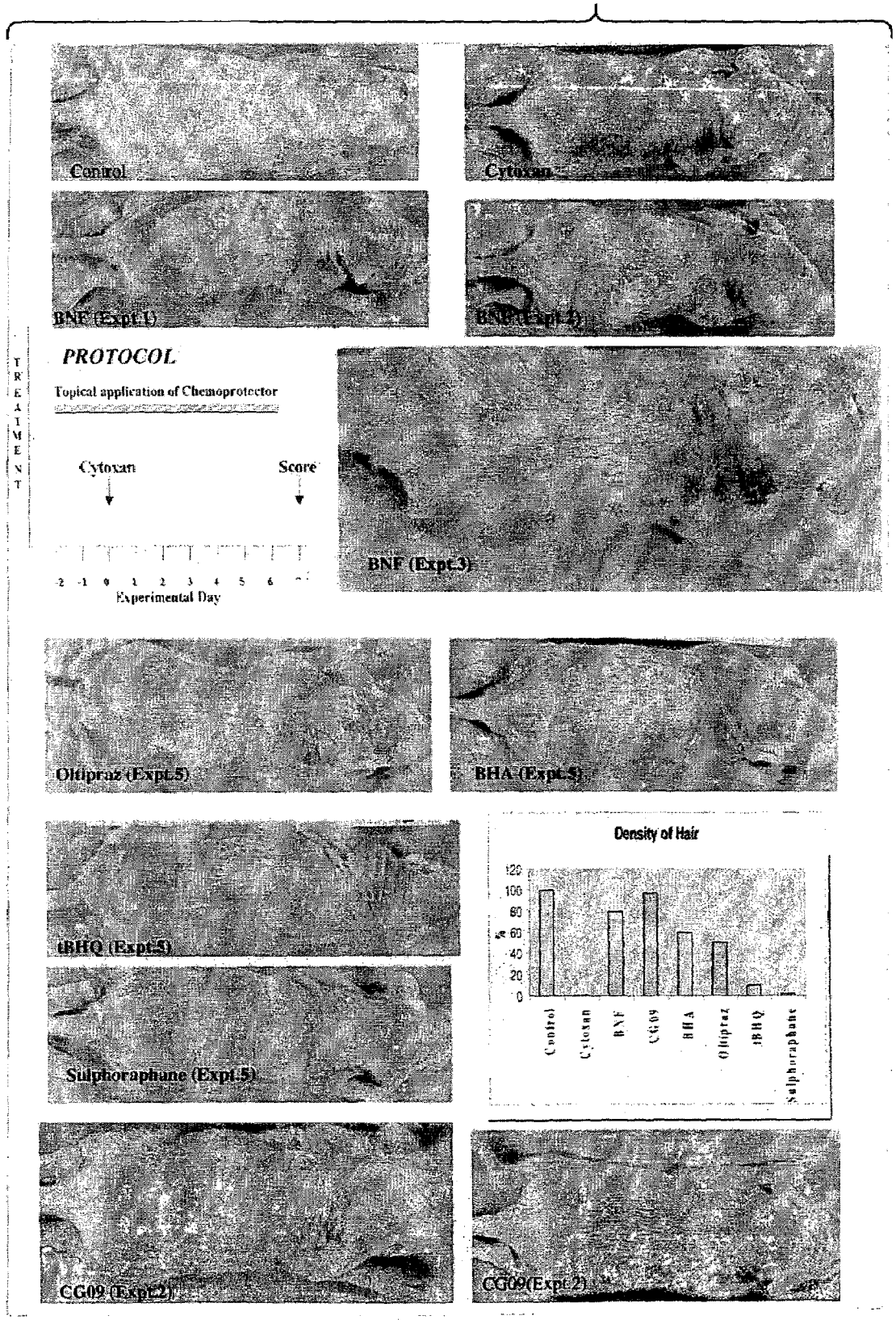
FIG. 1. Effect of chemoprotective inducing agents on hair loss in rat pups treated with cytoxan. Chemoprotective agents were prepared for delivery in a lipid droplet suspension or DMSO (Example 1) Upper inset: experimental protocol (Example 1); lower inset: histogram showing hair density in cytoxan-treated rat pups pre-treated with different chemoprotective inducing agents; photographs (left to right, upper to lower): control (untreated with cytoxan or chemoprotective inducer); cytoxan treated; cytoxan treated and pre-treated with (1) BNF (three panels), (2) Oltipraz (two panels), (3) BHA (one panel), (4) tBHQ (one panel), (5) sulphoraphane (one panel), and (6) CG09 (two panels).

The present invention provides compositions and methods for protecting non-cancerous, rapidly dividing cells in a patient's body from the toxic effects of chemotherapeutic agents or radiotherapy administered to the patient. In particular, the compositions and methods of the invention are designed for protecting epithelial cells. Most particularly, the targets are epithelial cells lining hair follicles and epithelial cells of the gastrointestinal tract.

Further applications of this invention are also anticipated at other cell sites that are affected when a patient is administered chemotherapy or radiotherapy. For instance, several skin pathologies have been observed in patients who receive intense regimens of chemotherapy and/or radiation therapy. These typically occur on the skin within the field of radiation therapy that is targeted to a tumor in an underlying organ. As one example, chest skin lesions often occur in patients irradiated for lung cancer. Another example is the occurrence of mucositis; i.e., development of mouth sores, in patients undergoing radiation therapy of the head and neck. Additionally, a phenomenon called "radiation recall" sometimes arises in patients previously irradiated without incident, wherein skin lesions occur when the patient is subsequently treated with cytoxan.

The skin lesions are generally variations of dermatitis; they can consist of dermis breakdown and ulceration (including the mouth sores mentioned above), generalized dermal rash, or scattered red lesions in a recurrently irradiated skin field. Formation of these cancer therapy-induced lesions is consistent with the high level of cell division that is always occurring within the epidermal layer of normal skin. The compositions of the present invention are contemplated to be of great utility in treating these skin fields that are at risk from recurrent radiation, as well as possible coincident systemic chemotherapy.

As illustrated in FIG. 3, the expression of a very large number of stress response genes is activated following exposure of the skin to any of several chemoprotective inducing agents. This group of activated genes encodes proteins directly involved in the phase II detoxification of drugs and reactive oxygen species, such as several GST isoforms, catalase and quinone reductase, to name a few, as well as proteins responsible for the export of drug molecules from cells, such as mdr-2, MRP, and the like. Also included are DNA repair enzymes. Because of this broad, up-regulated response, the inventors anticipate a resistance phenotype to a wide variety of drugs that includes alkylating molecules, but extends to many other cancer chemotherapy drug groups, such as antimetabolites, topoisomerase inhibitors, microtubule inhibitors, mitotic spindle poisons, antitumor antibiotics and vinca alkaloids. Even if the drug is not directly metabolized by one of the stress response gene products, it is still likely to be more rapidly exported from the cell by one or more of the up-regulated membrane drug export pumps. Examples of chemotherapeutic agents against which resistance in normal cells can be induced include, but are not limited to: altretamine, asparaginase, bleomycin, busulfan, carboplatin, cisplatin, carmustine, chlorambucil, cladribine, cyclophosphamide, cytarabine, dacarbazine, dactinomycin, daunorubicin, doxorubicin, etoposide, floxuridine, fludarabine phosphate, fluorouracil, hydroxyurea, idarubicin, ifosfamide, lomustine, mechlorethamine, nitrogen mustard, melphalan, mercaptopurine, methotrexate, mitomycin, mitoxantrone, paclitaxel, pentostatin, pliamycin, procarbazine, streptozocin, teniposide, thioguanine, thiotepa, vinblastine and vincristine.

Thus, the present invention makes use of the cell's ability to produce biological molecules that act as detoxifying agents for the cell. As used herein, the term "detoxifying agent" refers to an agent that, directly or indirectly, is capable of reducing or eliminating the toxic effect of one or more chemotherapeutic agents or of radiotherapy. Several categories of detoxifying agents are produced in cells. One category of agents acts by modifying the toxic compound to either reduce its toxicity or render it amenable to subsequent excretion from the cell. For example, most of the alkylating agents used in chemotherapy are lipophilic electrophiles that possess a major hydrophobic region. The absence of a direct exporting mechanism to remove these agents from cells results in a gradual intracellular accumulation of these hydrophobic electrophiles. Glutathione-S-transferases (GSTs) are well-known for their ability to inactivate a variety of antineoplastic alkylating drugs. GSTs are one group of enzymes that have an important role in protecting cells from the damage caused by electrophilic compounds. Another agent that acts by converting the chemotherapeutic agent to a less toxic form or a form that is more easily removed from the cell is aldehyde dehydrogenase. This molecule has been shown to be associated with increased resistance of cells to the effects of alkylating agents, including carboplatin and oxazaphosphorines, such as cyclophosphamide and 4-hydroperoxycyclophosphamide (Tanner et al., Gyn. Oncol. 65: 54-62, 1997; Bunting & Townsend, J. Biol. Chem. 271: 11884-11890, 1996). Aldehyde dehydrogenase catalyzes the oxidation of aldophosphamide, a key intermediate in the activation pathway of oxazaphosphorines, thereby detoxifying these agents (Sreerama & Sladek, Drug Metabolism and Disposition 23: 1080-1084, 1995).

Another category of detoxifying agents acts by facilitating transport of toxic agents (either modified for export as described above, or unmodified) out of cells. For instance, certain ATP-binding cassette (ABC) transporters have been identified in a wide variety of organisms, including mammals, that appear to act in this manner. Two well studied groups of ABC transporters, encoded by mdr and mrp genes, respectively, are associated with the multi-drug resistance phenomenon observed in mammalian tumor cells. The mdr genes encode a family of P-glycoproteins that mediate the energy-dependent efflux of certain lipophilic drugs (e.g., adriamycin, vinblastine, taxol) from cells. The mrp genes encode a family of transporters whose specificity overlaps that of the mdr gene product, but which also mediates the extrusion of a variety of organic compounds after their conjugation with glutathione.

It has been discovered in accordance with the present invention that elevation of one or more of these detoxifying agents in epithelial cells serves to protect the cells against the toxic effect of one or more of the chemotherapeutic agents enumerated above, as well as protecting them from damage during the course of radiation therapy. Thus, the present invention in its most basic aspect is drawn to delivering or otherwise increasing the production of such agents in epithelial cells before or during the early course of chemotherapy and/or radiotherapy, to protect the cells from cancer therapy-associated damage.

It should be noted, however, that most of the detoxifying agents listed above are enzymes. Delivery of polypeptides or genes encoding those polypeptides to a selected cell population, such that an effective amount of the detoxifying enzymes are present in those cells, is difficult and unpredictable. Accordingly, the present invention relies on inducing increased production of those enzymes in target cells by administration of small molecules that are known, or have been discovered, to induce increased production of one or more cellular detoxifying agents. These molecules are referred to herein as "chemoprotective inducers" or "chemoprotective inducing agents" or molecules. Thus, as defined herein, a "chemoprotective inducer" or "chemoprotective inducing agent" is an agent that, upon delivery to a cell, induces or increases production of the cell's endogenous detoxifying agents, as defined above.

It has been discovered in accordance with the present invention that chemoprotective inducers can be efficiently delivered to target cell populations, where they are capable of entering the cells and inducing or increasing production of one or more detoxifying enzymes by a variety of means, e.g., inducing increased expression of genes encoding the enzymes. The resultant benefit is the alleviation of symptoms associated with chemotherapy or radiotherapy; most notably, hair loss and gastrointestinal distress, as will be discussed in greater detail below.

The compositions of the invention comprise one or more chemoprotective inducers, which exert a detoxifying effect on one or more of the chemotherapeutic agents described above by inducing production of endogenous detoxifying molecules, and a delivery vehicle for delivering the chemoprotective inducers to the cells and tissues targeted for protection.

Chemoprotective inducing agent. For purposes of the present invention, a "chemoprotective inducer" may be any agent which, upon delivery to an epithelial cell, induces or increases production of a detoxifying molecule (as defined above) within the cell. Without intending to be limited by any explanation as to mechanism of action, the experimental results set forth herein suggest that these chemoprotective inducers are effective because they provide a mild oxidative stress that stimulates cells to produce a battery of stress-response molecules, such that those molecules are already increased in presence or activity when the more severe stress of chemotherapy or radiotherapy is imposed. This mechanism is sometimes referred to herein as "metabolic vaccination", due to its functional similarity to the vaccination process.

A second group of compounds, either alone or combined with the above compounds, to be included as "chemoprotective inducers" includes compounds that are functional ligands of the aryl hydrocarbon (Ah) receptor. In some cases, the hallmark induced expression of the cytochrome P45 1A1 gene resulting from an activated Ah receptor may provide a phase I metabolic step in detoxifying a drug, which will be followed by conjugation of the metabolite by one or more of the induced GSTs that are an integral part of the stress response gene battery. In essence, then, these compounds provide the opportunity for the cell to exert a metabolic "one-two punch" to remove a toxic drug from the cell. Examples of Ah receptor ligands that could be used in this capacity include, but are not limited to, indole-3-carbinol from cruciferous vegetables, and omerprazole (Jellink et al., Biochem. Pharmacol. 45: 1129-1136, 1993; Dzeletovic et al., J. Biol. Chem. 272: 12705-12713, 1997). Other suitable Ah ligands are known in the art.

Figure 15:
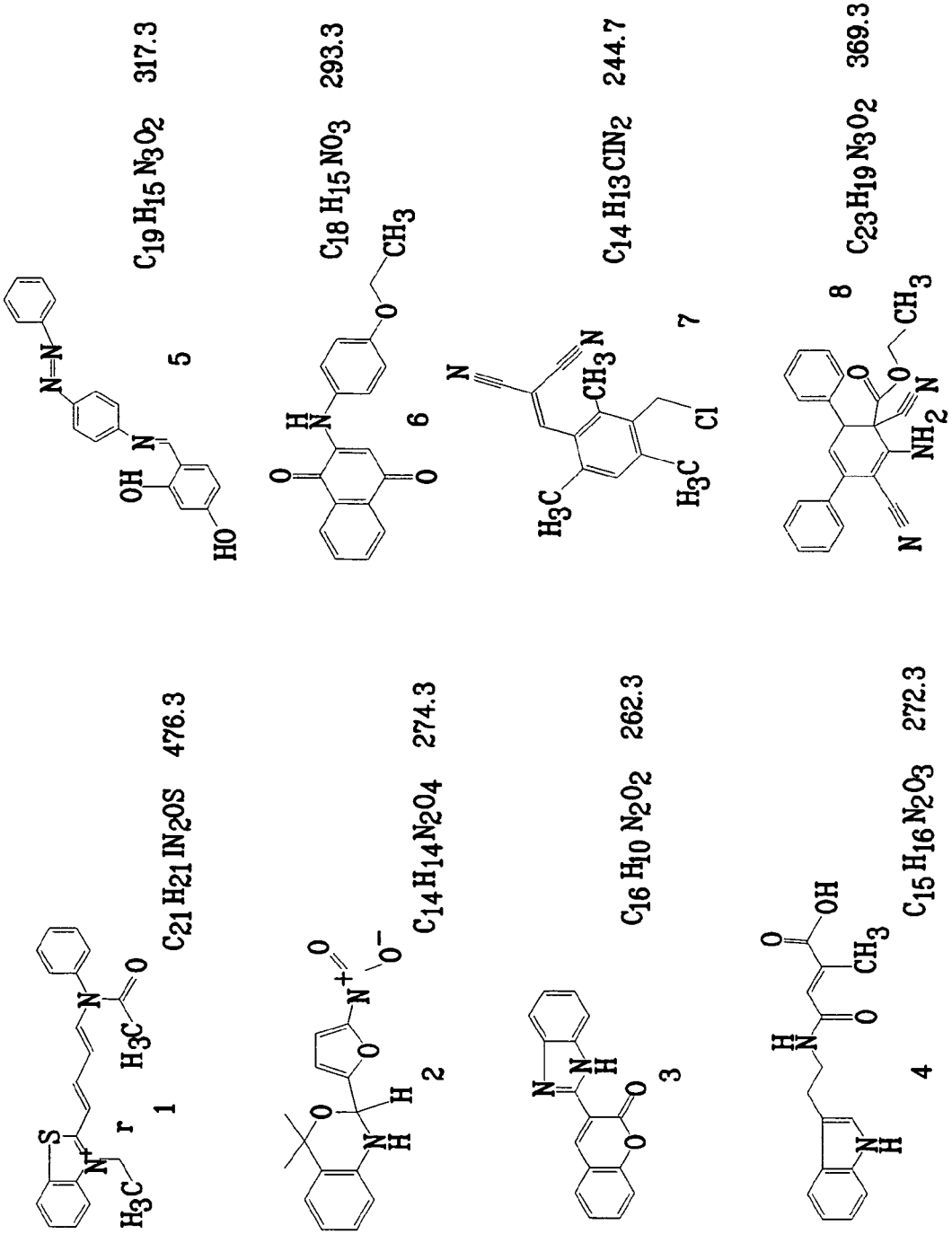
FIG. 15. Structures of certain molecules from ChemBridge library, which display chemoprotective inducing activity. Compound CG09 is Structure 1.

Many chemoprotective inducing agents known in the art are suitable for use in the present invention (e.g., DeLong et al., Cancer Res. 45: 546-551, 1985; Ioannou et al., Cancer Res. 42: 1199-1204, 1982; Chung et al., Cancer Res. 46: 165-168, 1986; Wattenberg et al., Cancer Res. 40: 2820-2823, 1980; and Kensler et al.; Cancer Res. 46: 3924-3931, 1986). Examples include, but are not limited to: 3-tert-butyl-4-hydroxyanisole (3-BHA), 2-tert-butyl-4-hydroxyanisole (2-BHA), 2-tert-butyl-1,4-dimethoxybenzene(methyl-BHA), 2-tert-butylhydroxyquinone (t-BHQ), 4-hdroxyanisole, ethoxyquin, α-angelica lactone, β-napthoflavone (β-NF), p-methoxyphenol and oltipraz. In addition to these, using methods disclosed herein in accordance with the invention, other chemoprotective inducers have been identified, including the molecules shown in FIG. 15, identified from a small molecule library from ChemBridge Corporation (San Diego, Calif.). As shown in FIG. 15, the most potent chemoprotective inducing agent identified thus far is CG09 from the Chembridge library (Structure 1 in FIG. 15).

Some of the molecules listed above (e.g, BHA) are used as chemical antioxidants in the food industry. However, as appreciated in this invention, their effect is as oxidants upon metabolism in the body. For instance, when BHA is administered to mammals, it is metabolized to yield tert-butylhydroquinone (t-BHQ) as a primary metabolite. Like most hydroquinones in cell systems, t-BHQ spontaneously undergoes cyclic conversion between the quinone and hydroquinone forms, i.e., redox cycling in the cells. A side-product of redox cycling is the formation of one or more forms of oxygen free radical. The cells sense these oxygen free radicals as an environmental stress, which triggers expression of stress-response genes. It is in this manner that chemical antioxidants such as BHA may become effective oxidants in the cell, so as to act as chemoprotective inducers as defined herein.

Delivery vehicle. The compositions of the invention also comprise a delivery vehicle. The main function of the delivery vehicle is to carry the chemoprotective inducer(s) to the cell population or tissue targeted for protection from the chemotherapeutic agents.

Delivery of organic and biological substances via the skin using a noninvasive carrier system has many attractions, including patient acceptability due to the noninvasiveness of the procedure and avoidance of gastrointestinal disturbances and first-pass metabolism of the delivered molecule. However, the major problem in dermal delivery is the low penetration rate of most substances through the barrier of the skin stratum corneum. The skin consists of two layers, dermis and epidermis. The dermis consists of connective tissue, nerves, blood and lymph vessels, hair follicles, sebaceous and sweat glands. Epidermis consists of cells in several stages of differentiation; during this differentiation the cells migrate from the basal layer to the surface and cornify to form stratum corneum. The lipid matrix of the stratum corneum is formed of double-layered lipid membranes composed of cholesterol, free fatty acids and ceramides. Although the stratum corneum is considered to be the main barrier to percutaneous absorption, it is also regarded as the main pathway for penetration. Therefore compounds that loosen or fluidize the lipid matrix of the stratum corneum may enhance the permeation of substances through the skin. This is usually achieved by utilizing carrier molecules like albumin conjugates, lecithins, glycoproteins, polysaccharides and liposomes.

Among these choices, liposomal formulations offer several advantages over more conventional formulations. The major advantages are: (1) reduced serious side effects and incompatability from undesirably high systemic absorption; (2) significantly enhanced accumulation of the delivered substance at the site of administration due to high compatability of liposomes with stratum corneum; (3) ready incorporation of a wide variety of hydrophilic and hydrophobic molecules into the skin; (4) protection of the entrapped compound from metabolic degradation; and (5) close resemblance to the natural membrane structure and their associated biocompatibility and biodegradability.

Liposomes may be defined as spherical concentric fluid mosaics made from highly precise self-assembly of phospholipid molecules which are formed when phospholipids are dispersed in aqueous medium. When lipids are placed in aqueous medium, the hydrophilic interaction of the lipid head groups with water results in the formation of multilamellar and unilamellar systems or vesicles which resemble biological membranes in the form of a spherical shell. These basic liposomes are sometimes referred to as "conventional liposomes." Several other types of liposomal preparations exist, including (1) sterically stabilized liposomes, which are surface coated with an inert hydrophilic polymer, such as polyethylene glycol; (2) targeted liposomes, to which are attached targeting ligands, such as antibodies or fragments thereof, lectins, oligosaccharides or peptides (as discussed below, choleratoxin B (CTB) is used to target liposomes to the gastrointestinal epithelium); and (3) reactive or "polymorphic" liposomes, which change their phase and structure in response to a particular interaction (this group includes liposomes sensitive to ions (pH, cations), heat and light, among other stimuli. For a review of the different types of liposomes listed above, see Chapter 6 of D. Lasic, *Liposomes in Gene Delivery*, CRC Press, 1994.

In order to achieve efficient delivery of a chemoprotective molecule into the skin, various formulations of liposomes (phospholipid-based vesicles, cationic liposomes, nonionic liposomes, non ionic/cationic liposomes, pegylated liposomes, PINC polymer, and propylene glycol and ethanol mixture (commonly used vehicle for administering minoxidil), and nonionic liposome/propylene glycol and ethanol mixtures were tested (see Examples). It was determined that nonionic liposomes or a mixture of nonionic liposomes and propylene glycol/ethanol are the most effective transdermal carriers.

Reactive liposomes may be preferred for other embodiments of the present invention. Inclusion of cationic amphiphiles as a minor component of liposomes facilitates the association with negatively charged solutes, the rapid binding of liposomes to the cell surface, and the cellular uptake of liposomes. pH-sensitive liposomes have been developed to improve the efficiency of the cytoplasmic delivery of antitumor drugs, proteins, and nucleic acids. Most pH-sensitive liposomes have been prepared using phosphatidylethanolamine (PE). PE alone does not form liposomes and is prone to form the inverted hexagonal phase ($H_{II}$). However, liposomes can be prepared by adding another bilayer-stabilizing, amphiphilic lipid component to PE. Titratable amphiphiles having a carboxyl group have been used as a component for the preparation of pH-sensitive liposomes. Because the ability to stabilize a bilayer membrane by these titratable amphiphiles decreases under acidic conditions, destabilization results in the fusion of the liposomes. pH-sensitive liposomes are stable at physiological pH, and are internalized by cells through an endocytic pathway, which exposes the liposomes to an acidic pH. Liposomes within the endosome are destabilized and possibly fuse with the endosome membrane, resulting in release of their contents into the cytoplasm without degradation by lysosomal enzymes.

In other embodiments of the invention, sterically stabilized, inert liposomes are particularly suitable. In still other embodiments, targeted liposomes may be used to advantage.

In other embodiments of the invention, particularly for administration of chemoprotective inducing agents to the epidermis, lipid-based "creams" are particularly well suited. Creams are generally formulated to include water, alcohol, propylene glycol, sodium lauryl sulfate and white wax. In alternative formulations, they include water, alcohol, glycerol, phosphatidyl choline, lysophosphatidyl choline and triglycerides.

Other delivery vehicles are also suitable for use in the present invention, particularly for administration of detoxifying agents to the gastrointestinal lumen. Nonlimiting examples include: (1) oils such as vegetable oils or fish oils (which can be encapsulated into standard gel capsules); and (2) emulsions prepared by dispersing polyoxyethylene ethers, e.g., 10-stearyl ether (Brij 76) in aqueous buffer.

Other examples of delivery vehicles suitable for the GI lumen include biodegradable microparticles (0.1-10 µM diameter) of polylactic polyglycolic acid, which have been used to deliver proteins to Caco-2 cells as an in vitro model system for gastrointestinal uptake via oral drug delivery (Desai et al., Pharm. Res. 14: 1568-1573, 1997). Others have shown significant uptake of proteins carried by polystyrene particles into cells lining the small intestine of the rat (Hillery et al., J. Drug Targeting 2: 151-156, 1994). Indeed, delivery of protein-containing microparticles has been reported from the GI lumen all the way to the submucosal vasculature (Aphramaian et al., Biol. Cell 61: 69-76, 1987). Therefore, such polymeric microparticles are quite suitable for oral delivery of chemoprotective inducing agents to gastrointestinal epithelial cells, which are found on the surface of the GI lumen.

Administration of pharmaceutical preparations comprising chemoprotective inducers. Depending on the cell population or tissue targeted for protection, the following modes of administration of the compositions of the invention are contemplated: topical, oral, nasal, ophthalmic, rectal, vaginal, subcutaneous, intraperitoneal and intravenous. Because targeted delivery is contemplated, certain of these modes of administration are most suitable for targeted delivery vehicles (e.g., CTB- or antibody-studded liposomes).

The compositions of the present invention are generally administered to a patient as a pharmaceutical preparation. The term "patient" as used herein refers to human or animal subjects (animals being particularly useful as models for clinical efficacy of a particular composition). Selection of a suitable pharmaceutical preparation depends upon the method of administration chosen, and may be made according to protocols well known to medicinal chemists.

The pharmaceutical preparation comprising the compositions of the invention are conveniently formulated for administration with a acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of a particular composition in the chosen medium will depend on the hydrophobic or hydrophilic nature of the medium, in combination with the specific properties of the delivery vehicle and active agents disposed therein. Solubility limits may be easily determined by one skilled in the art.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the compositions to be administered, its use in the pharmaceutical preparation is contemplated.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of the chemoprotective inducing agent(s) calculated to produce the desired protective effect in association with the selected pharmaceutical carrier. Procedures for determining the appropriate dosage unit are well known to those skilled in the art.

Dosage units may be proportionately increased or decreased based on the weight of the patient. Appropriate concentrations for achieving protection of a target cell population or tissue from the toxic effect of a particular chemotherapeutic agent may be determined by dosage concentration curve calculations, as known in the art.

As one example, for topical applications, the chemoprotective inducers may be used at concentrations ranging from 5-100 mM in an appropriate carrier (e.g., liposome emulsion) applied to the scalp or other dermal site. This dosage is arrived at from results of experiments using a rodent model (see Examples 1-3), and the range of dosages is a function of results obtained from experiments using several different molecules that ranged in dose effectiveness. The volume of material applied to the skin ranges by size of surface area to be covered; e.g., scalp treatment for young children requiring 3-5 ml, the amount being increased in adults to 10-20 ml per application.

As another example, for gastrointestinal, administration, the oral dose of the chemoprotective inducer in an appropriate medium (e.g., liposome emulsion) is normalized to the lumenal surface area of the stomach and duodenum. This would assume that the patient consumes the material on an empty stomach upon rising in the morning.

Regimens for administration of pharmaceutical preparations. The pharmaceutical preparation comprising the compositions of the invention may be administered at appropriate intervals, before, during, or after a regimen of chemotherapy and/or radiotherapy. The appropriate interval in a particular case would normally depend on the nature of the chemotherapy or radiotherapy and the cell population targeted for protection.

For instance, for prevention of chemotherapy-induced alopecia, liposomes or other delivery vehicles containing chemoprotective inducing agents can be formulated to be delivered, e.g., as a topical cream, to the scalp of a patient prior to scheduled administration of chemotherapy. By protecting the epithelial cells that line the exposed surface of hair follicles from the chemotherapy drug, the loss of hair commonly associated with cancer chemotherapy can be prevented. As described in greater detail in the examples, the topical formulation preferably is initiated 1-5 days prior to chemotherapy, to ensure that the induced detoxifying gene products are fully activated in the follicular epithelial cells when the chemotherapy is administered. The formulation may then continue to be applied during the course of chemotherapy.

For protection of the gastrointestinal epithelium, chemoprotective inducers are formulated to be delivered by mouth to a patient prior to scheduled administration of chemotherapy. Administration of the protective formulation in the 1-5 days prior to the infusion of the chemotherapeutic agent thus confers protection to susceptible epithelial cells. For example, the patient would be instructed to consume a "shake" containing the chemoprotective inducer/liposome emulsion before breakfast in the morning, in the 1-5 days preceding chemotherapy. As a result, levels of the stress response gene products would be present at their induced maximum at the time when the chemotherapy drugs permeate the GI lumenal epithelium.

Identification of novel chemoprotective inducing agents. As discussed above, a variety of molecules are known to induce stress response genes in cells, thereby providing the chemoprotective inducing effect utilized in the present invention. However, it would be an advance in the art to devise a simple method for identifying new chemoprotective inducers with equivalent or superior activity. Hence, the present invention also provides a rapid and simple assay system for screening candidate molecules for their ability to induce or increase the production or activity of one or more stress response molecules capable of detoxifying a cell of damaging chemotherapeutic agents or biproducts of radiation therapy. The method is described in detail in Example 4. The assay is based on the demonstration that the electrophile responsive element (EpRE) mediates the induced expression of phase II detoxifying enzymes and oxidative stress proteins, which constitutes an important mechanism of cellular protection from a variety of environmental agents (Wasserman et al., Proc. Natl. Acad. Sci. USA 94: 5361-5366, 1997). The assay utilizes a DNA construct comprising a reporter gene operably linked to a promoter, adjacent to which are inserted one or more EpRE regulatory elements. Cells are transformed with the DNA construct, and clones selected which display low presence or activity of the expressed reporter gene product (negative control), with inducible high presence or activity of the reporter gene product upon exposure of the cells to a known inducer of phase II detoxifying enzymes (positive control). The cells are then exposed to candidate test compounds, and the level of expression of the reporter gene is measured. This assay can be assembled in a multiple well system for the simultaneous testing of many test compounds.

In a preferred embodiment of the invention, the reporter gene encodes a green fluorescent protein, as described in Example 4, under control of a thymidine kinase promoter and a concatemer of EpRE regulatory elements.

Also provided in accordance with the invention is a kit to facilitate practice of the screening assay. The kit comprises the DNA construct and instructions for carrying out the assay. In addition, the kit optionally may comprise a cultured cell suitable for transformation, reagents to use as controls in the assay, reagents for detecting the amount of expression of the reporter gene, and other various culture media or biochemical reagents, as appropriate.

Use of chemoprotective inducers to prevent cancer. Though the etiology of cancer is not thoroughly understood, it is well known that certain chemicals or environmental agents act as mutagens and carcinogens. For this reason, the present invention also contemplates the use of the chemoprotective inducer formulations as a cancer preventative. Prophylactic consumption of these agents as part of a daily diet regime will result in chronic induced expression of chemoprotective genes in a host of normal organs, such as stomach and intestines, as well as non-GI tissues such as breast. The chronic increase in detoxifying cellular proteins will better enable those cells to detoxify chemical carcinogens encountered in everyday life, such carcinogens commonly arising from smoking and food by-products.

The following examples are provided to illustrate the invention. They are not intended to limit the invention in any way.

EXAMPLE 1

Prevention of Chemotherapy-Induced Alopecia by Topical Application of Molecules that Induce Expression of Chemoprotective Gene Products The inventors postulated that drug induced alopecia could to a large extent be successfully prevented by selective protection of hair follicles by expressing chemoprotective gene products such as GSTs, MRP, MDR, ALDH3 and the like, that are known to protect cells against cytotoxicity. Combined, increased expression of MRP and GST P1 has been found to confer high level resistance to the cytotoxicities of anticancer drugs (Morrow et al, 1998); however, expression of either MRP or GST alone was found to be less successful as these gene products work in synergy to protect cancerous cells against cytotoxicity by their coordinated action in the removal of the anticancer drugs from cells.

The experiments set forth in this example were designed with the idea of overexpressing these protective genes in hair follicle cells by delivering molecules that are known to induce the expression of the above mentioned chemoprotective genes. Alopecia was induced in 7 day old rat pups by administering cytoxan (FIG. 1 inset). Before and during cytoxan administration, the rats were treated with chemoprotective molecules using nonionic liposomes as the vehicle for entry into the hair follicles, and the efficacy of each of the chemoprotectants in the prevention of alopecia was determined.

Materials and Methods:

Induction of alopecia by cytoxan (CTX). Lactating Sprague Dawley rats with 12 pups per mother were purchased from Harlan Sprague Dawley. To produce CTX induced alopecia, several concentrations (35, 40 45 $\mu$g/gm body weight) of CTX in water were injected i.p. in to 7 day old pups. Seven days after CTX treatment the pups were examined to determine the degree of hair loss. The pups were gently brushed on the back to remove the loose hair sticking onto the skin and photographed. The density of hair on the pups was then determined. 100% hair density represents that found on the untreated control pups while 0% represented pups with total hair loss. It was observed that 40 $\mu$g/gm of CTX was sufficient to induce 100% hair loss on 7 day old pups and this concentration was used in subsequent experiments.

Treatment with chemoprotectants; preparation of nonionic liposomes as the vehicle for delivery. The nonionic liposome preparations contained glyceryl dilaurate (GDL), Cholesterol, Polyoxyethylene-10-stearyl ether (POE-10) at a weight percentage ratio of 58:15:27. The lipid mixture also contained 1% $\alpha$-tocopherol. Appropriate amounts of the lipids were mixed (100 mg/ml total lipid) and melted at 70° C. in a sterile polystyrene tube. The lipid mixture was drawn into a sterile syringe. A second syringe containing sterile PBS was preheated to 70° C. and connected via a 2-way stopcock to the lipid phase syringe. The aqueous phase was then slowly injected into the lipid phase syringe. The mixture was rapidly passed back and forth between the two syringes while being cooled under running cold tap water until the mixture reached room temperature. The final preparation was examined under a microscope to assure integrity and quality of the liposomes. Immediately before use, the liposomes were sonicated at RT for 2 min and mixed with an equal volume of the chemoprotectant in a suitable solvent (typically, DMSO) and incubated at RT for 45 min.

Several nonionic liposomal preparations were prepared containing the following chemoprotectants:

5 mM B-NF
10 mM B-NF
15 mM B-NF
5 mM CG09
10 mM CG09
15 mM CG09
20 mM CG09
25 mm BHA
50 mM BHA
25 mM tBHQ
50 mM tBHQ
5 mM sulphoraphane
10 mM sulphoraphane
15 mM oltipraz
20 mM oltipraz The liposome formulations were applied using a pipetman onto a 1 square cm area of the dorsal back of 7 day old rat pups skin starting from day—2 of the experiment. On day 0 of the experiment, the animals were injected with 40 µg/gm CTX. The application of the liposome preparations continued until day 6 of the experiment. The control animals received only the empty liposomes. On day 7 of the experiment, the animals were scored to determine the degree of alopecia. The pups were gently rubbed on their backs to remove the loose hair and were photographed. FIG. 1 illustrates the effect of the chemoprotective molecules on the prevention of hair loss.

Results:

Among the known chemoprotective compounds, B-NF had an 80% protective effect followed by BHA (60%), Oltipraz(50%), tBHQ (10%) and sulphoraphane (5%). The newly discovered compound CG09 showed the highest level of protection at ~97% (FIG. 1 inset). The hair texture was also found to be comparable to that of untreated rat pups. It was observed that, when the chemoprotective molecules were delivered using DMSO as the carrier, although the pups retained their hair after CTX treatment, their skin was rough and scaly. The minoxidil carrier, a propylene glycol:ethanol: water mixture, failed to work as an effective carrier for these chemoprotective molecules. Alopecia in the pups treated with B-NF or CG09 in the minoxidil vehicle was as severe as the untreated CTX-treated rat pups (FIG. 2).

EXAMPLE 2

Effect of Small Molecule Inducers of Chemoprotective Genes on Chemoprotective Gene Expression in Skin To elucidate the basic mechanism underlying this protective effect of B-NF and CG09, we studied the expression levels of chemoprotective genes such as GSTs, MDR, MRP and ALDH3, under the same topical treatment conditions as described in the previous example.

In brief, rat pups were treated with either CTX or B-NF and at different time intervals skin samples were collected and total RNA was extracted from them. The RNA was reverse transcribed to form the respective cDNAs in the presence of $^{32}P$ dATP using primers specific for stress-related genes. The radiolabeled cDNA synthesized was used to probe a rat stress gene cDNA expression array consisting of 207 stress-related genes (Clontech) according to the manufacturer's protocol. The hybridized membrane was exposed to a phosphorimager screen and the image obtained was aligned with an orientation grid to identify the genes that are expressed. Images from control, CTX-treated and B-NF-treated animals were compared to determine the changes, if any, in the expression pattern of chemoprotective genes under these experimental conditions.

Figure 6:
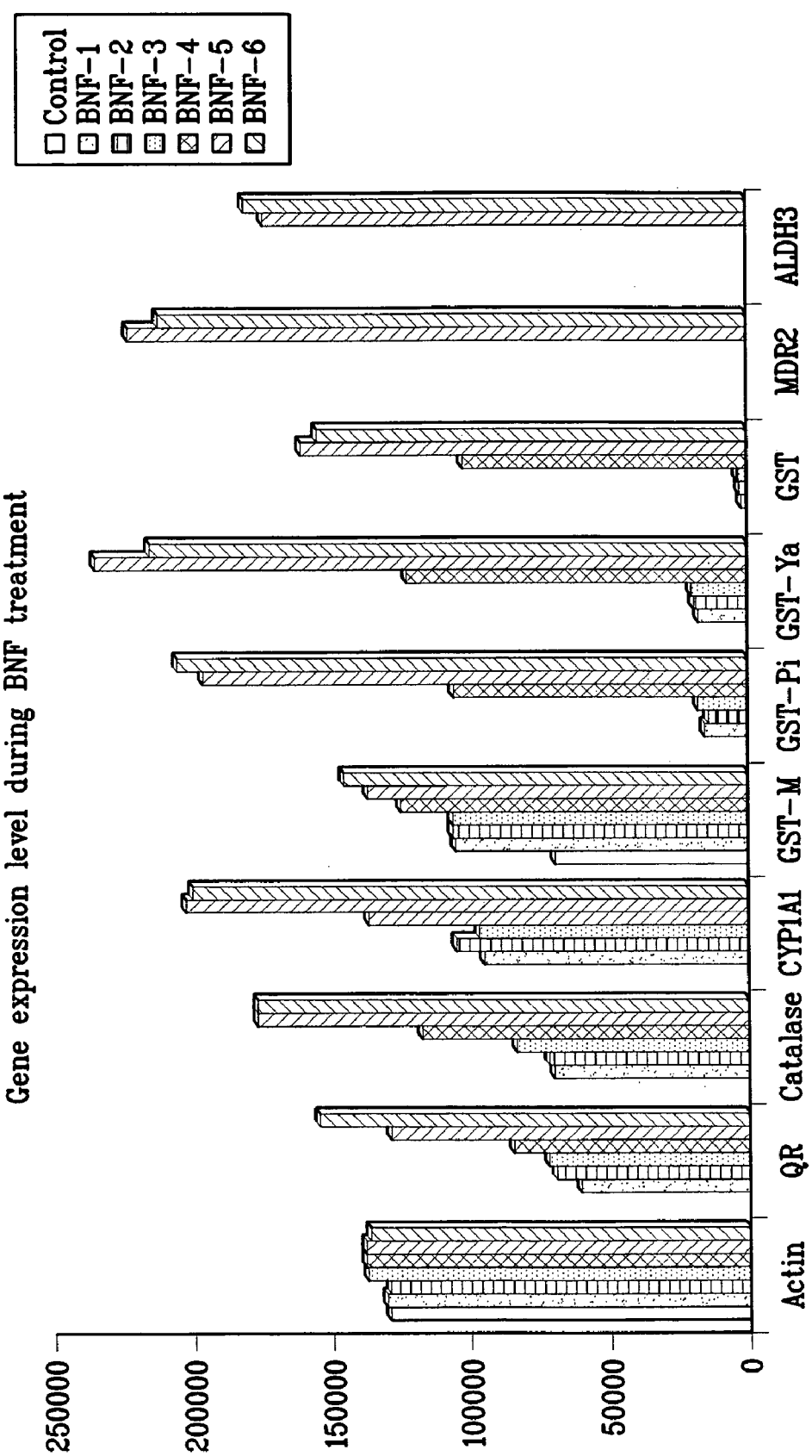
FIG. 6. Histogram showing expression of a series of genes in rats, whose expression in rat dermal cells is induced in the 1-6 (BNF1-BNF6) days following daily application of a βNF/nonionic liposome emulsion to the skin. Bars show, from left to right, control and BNF1-BNF6.

FIG. 3 depicts the expression pattern of stress genes in rat pups treated with B-NF and cytoxan. Topical administration of 15 mM B-NF to rat pups for 5 days resulted in a significant increase in the expression level for GST-PI, GST-Mu2, GST-Ya, and GST (rat homolog of human) when compared to rat pups treated with cytoxan. FIG. 6 shows a series of genes whose expression in rat dermal cells, the majority of which are follicular cells, is induced in the 1-6 days (β-NF1-β-NF6, plateauing on day 5) following daily application of the βNF/ nonionic liposome emulsion to the rat pup's skin. Noteworthy points from the graph: (1) β-NF or CG09 were applied only on the day before cytoxan, but nevertheless, a substantial protective effect was achieved; (2) the data provide a strong argument for starting the topical scalp treatment on day—5 with cytoxan administered on day 0, and then continuing topical treatment through several days post cytoxan to enable cytoxan to be cleared from the patient's body; (3) the list of genes whose expression is induced (i.e., the names below the vertical bars) makes it clear why the toxicity of cytoxan is nearly eliminated in the follicular cells. These genes, several GSTs and aldehyde-dehydrogenase, are known to metabolize and detoxify cytoxan and other alkylating drugs. The elevation of mdr-2 gene, expression strongly suggests that a resistance or protection phenotype in the follicular cells will be displayed when the animals are treated with adriamycin, cytosine arabinoside and other drugs that are known to induce alopecia and which are also known to be substrates for the mdr-2 membrane efflux pump.

Figure 7:
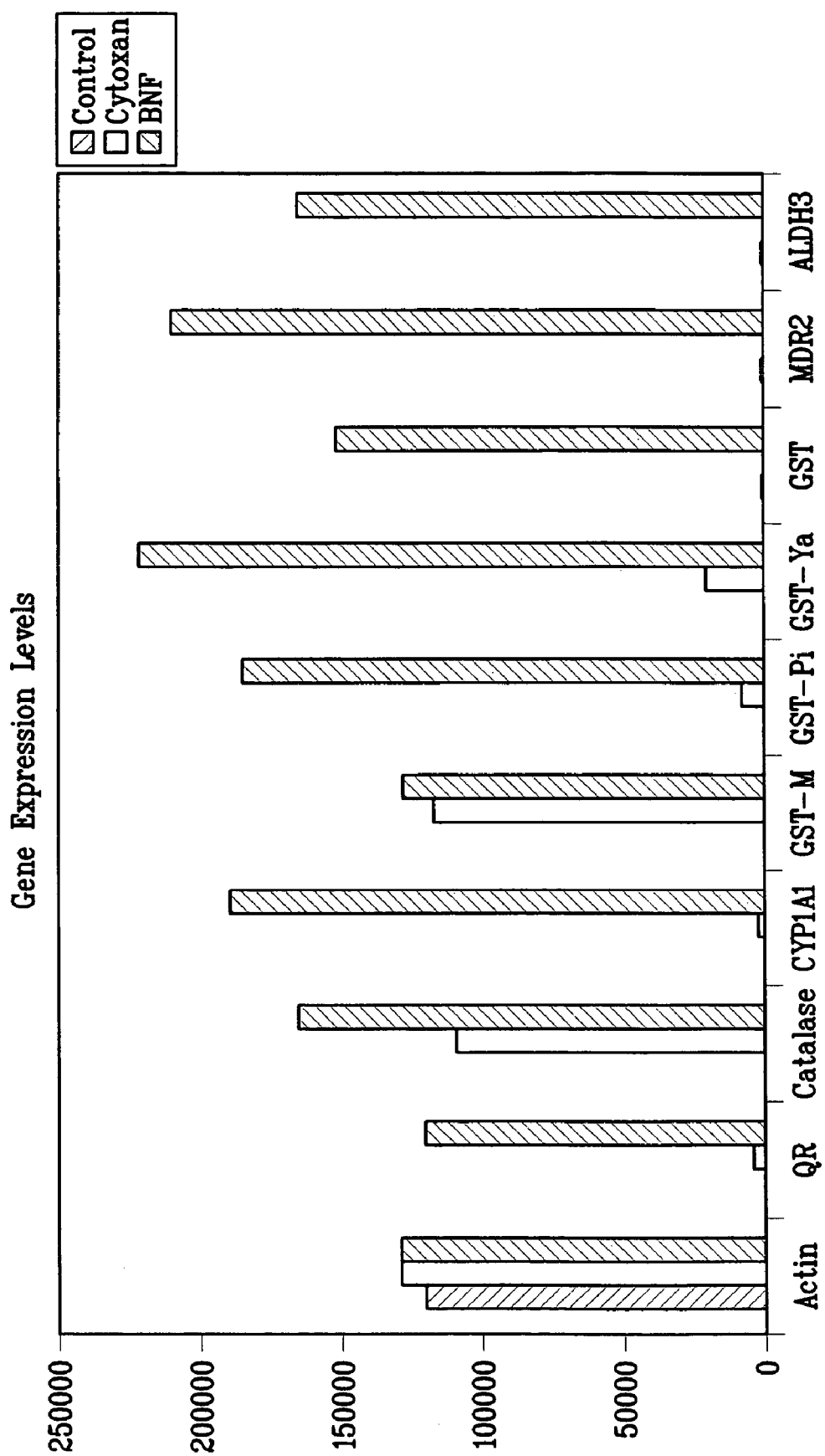
FIG. 7. Histogram showing expression of a series of genes in rats, whose expression in rat dermal cells is induced 5 days following daily application of a βNF/nonionic liposome emulsion to the skin. Comparison is made to gene expression following a single intraperitoneal injection of cytoxan. From left to right: control, cytoxan, βNF.

FIG. 7 shows the stress-response genes induced in dermal tissue on the fifth day of β-NF treatment (only) or on the fifth day following systemic administration of cytoxan (only). Systemic cytoxan administration induces a subset of stress response genes in dermal cells. Unfortunately, cytoxan is long cleared and its damage done before the cytoxan-induced stress response genes are significantly expressed. Accordingly, the present invention utilizes the "molecular vaccination" technique of applying a more moderate stress inducer, such as β-NF, 1-5 days prior to the administration of the chemotherapeutic agent, so that expression and detoxification activity of these enzymes is at a peak when the chemotherapeutic agent is delivered.

EXAMPLE 3

Identification of Carriers for Delivery of Chemoprotective Gene Inducers to Epithelial Cells In order to achieve efficient delivery of a chemoprotective molecule into the skin, studies were conducted using various formulations of liposomes (phospholipid-based vesicles, cationic liposomes, nonionic liposomes, non ionic/cationic liposomes, pegylated liposomes, PINC polymer, and propylene glycol and ethanol mixture (commonly used vehicle for administering minoxidil). First, these formulations were used to entrap reporter genes such as those encoding the marker proteins Luciferase or β-galactosidase, or a fluorescent probe (Nile Red), and their delivery was tracked in the target tissue by the functional assay of the marker proteins delivered or fluorescence emission in the case of Nile Red. The liposomes were prepared as set forth below.

Phospholipid based vesicles. The preparation contained the following lipid mixtures in a 1:0.5:0.1 molar ratio:
1. DSPC: Cholesterol: DOTAP
2. DOPE: Cholesterol: DSPC
3. DOPE-2000: Cholesterol: DSPC The lipids were dissolved in chloroform and evaporated in a rotoevaporater at 50° C. The dried lipid film was hydrated with HEPES buffer containing DNA (β-gal or Luciferase) or one mg of Nile Red at RT for 30 min. The resulting suspension was subjected to five cycles of freezing and thawing. The final suspension was passed through 0.22 μm filter seven times. The vesicles were stored at 4° C.

Nonionic liposomes. The nonionic liposomre preparations contained glyceryl dilaurate (GDL), cholesterol, polyoxyethylene-10-stearyl ether (POE-10) at a weight percentage ratio of 58:15:27. The lipid mixture also contained 1% α-tocopherol. Appropriate amounts of the lipids were mixed (100 mg total lipid) and melted at 70° C. in a sterile polystyrene tube. The lipid mixture was drawn into a sterile syringe. A second syringe containing sterile PBS was preheated to 70° C. and connected via a 2-way stopcock to the lipid phase syringe. The aqueous phase was then slowly injected into the lipid phase syringe. The mixture was rapidly passed back and forth between the two syringes while being cooled under running cold tap water until the mixture reached room temperature. The final preparation was examined under a microscope to assure integrity and quality of the liposomes. Immediately before use, the liposome preparation was sonicated for 2 min at RT and an equal volume of reporter DNA (250 μg) was added and incubated at RT for an hour.

Nonionic/Cationic liposomes. The nonionic/cationic preparations contained GDL, POE—10, cholesterol, DOTAP (1,2 dioleyloxy-3(trimethylammonio) propane at a weight percent ratio of 50:23:15:12 in a 100 mg/ml preparation. Appropriate amounts of the lipids were mixed and melted in a polystyrene tube at 70° C. and drawn into a syringe preheated to 70° C. A second syringe containing sterile PBS was preheated to 70° C. and connected to the lipid phase syringe via a 2-way stopcock. The aqueous phase was slowly injected into the lipid phase syringe. The mixture was rapidly passed back and forth between the two syringes while being cooled under cold tap water until the mixture reached room temperature. Immediately before use, the liposomal suspension was sonicated for 2 min at RT and an equal volume of (DNA 250 μg) and nonionic/cationic liposomes were mixed and incubated at RT for 1 hour.

PINC (Protective, Interactive and Non Condensing) polymers. Formulations were made by mixing 70% PVP, 30% Vinyl Acetate and 250 μg plasmid DNA in 0.9% NaCl and incubating at RT for 15 min.

PG (propylene glycol): Ethanol—plasmid DNA complex (Minoxidil vehicle). 250 μg of plasmid DNA was mixed with 60% PG, 20% Ethanol and 20% water and incubated at RT for 15 min before use.

To determine the efficiency of entrapment of the reporter genes, a DNA intercalation study with ethidium bromide was done to ensure that the DNA added has been entrapped in the liposomes. In brief, one ml of ethidium bromide (2 μg/ml) was added to an aliquot of the liposome preparation containing DNA and mixed for three seconds in a vortex mixer. As positive and negative controls, DNA and ethidium bromide and ethidium bromide alone were used. The ethidium bromide based fluorescence of all samples was monitored in a fluorimeter at an emission wavelength of 595 nm.

In vivo Experiments on Rat Pups. Animal experiments were conducted on six day old Harlan Sprague Dawley rat pups. 100 μl of the liposome formulation containing the luciferase gene, or β-galactosidase gene, or one mg Nile Red (Fluorescent probe) was applied at 30 min intervals onto a 1 square cm area of the back dorsal skin. Control pups received only the empty liposomes. After 24, 48 and 72 hours, the pups were sacrificed and the treated skin section was dissected out and used to analyze the expression of reporter genes or the level of fluorescent probe.

In situ β-galactosidase assay. A portion of the skin section was embedded in OCT, sectioned and fixed as 5 μm strips onto super frost slides with ice cold 1% formaldehyde, 0.2% glutaraldehyde, 2 mM MgCl2 in PBS. The fixed tissues were washed at RT for 2 hours in three changes of PBS containing 2 mM $MgCl_2$, 0.1% sodium deoxycholate, 0.02% NP40. These were subsequently stained in the dark at 37° C. for 16 hours in 2 mg/ml 4-Cl-5-Br-3-indlyl-β-galactopyranoside (X-Gal), 5 mM potassium ferricyanide, 5 mm potassium ferrocyanide, 2 mm MgCl2, 0.02% NP40 and 0.1% sodiumdeoxy cholate in PBS. At the end of the incubation period, the slides were washed with PBS and counterstained in hemotoxylin and eosin for histological examination.

Preparation of tissue homogenate. The dissected skin section was cut into small pieces and homogenized in 2 ml of reporter lysis buffer (Promega) using a Polytron homogenizer. The homogenate was centrifuged at maximum speed for 15 min and the supernatant was used for further analyses. Protein content of the homogenate was determined using the BCA (Pierce) method.

Quantitative analysis of β-galactosidase activity. β-galactosidase activity was measured by adding an aliquot of the tissue homogenate to an equal volume of 2× assay buffer (Promega), which contains the substrate (o-nitrophenyl-β-D-galactopyranoside). Samples were incubated for 30 min at 37° C. during which time the β-galactosidase enzyme hydrolyzes the colorless substrate to 0-nitophenol, which is yellow. The reaction was terminated by the addition of 1M sodium carbonate and the absorbance was measured at 420 nm in a spectrophotometer. The activity was expressed as units/mg protein.

Quantitative analysis of Luciferase activity. Luciferase activity was measured in the tissue homogenate using the Dual Luciferase assay Kit (Promega) following the manufacturer's instructions. In brief, to 100 μl of the sample was added 100 μl of the Luciferase assay buffer containing the substrate and the light emitted immediately after the addition of Stop&Glo buffer was measured in a luminometer. The activity was expressed as RLU/mg protein.

Nile Red. Fluorescence emission of Nile Red was observed under a fluorescent microscope on skin sections.

Figure 4:
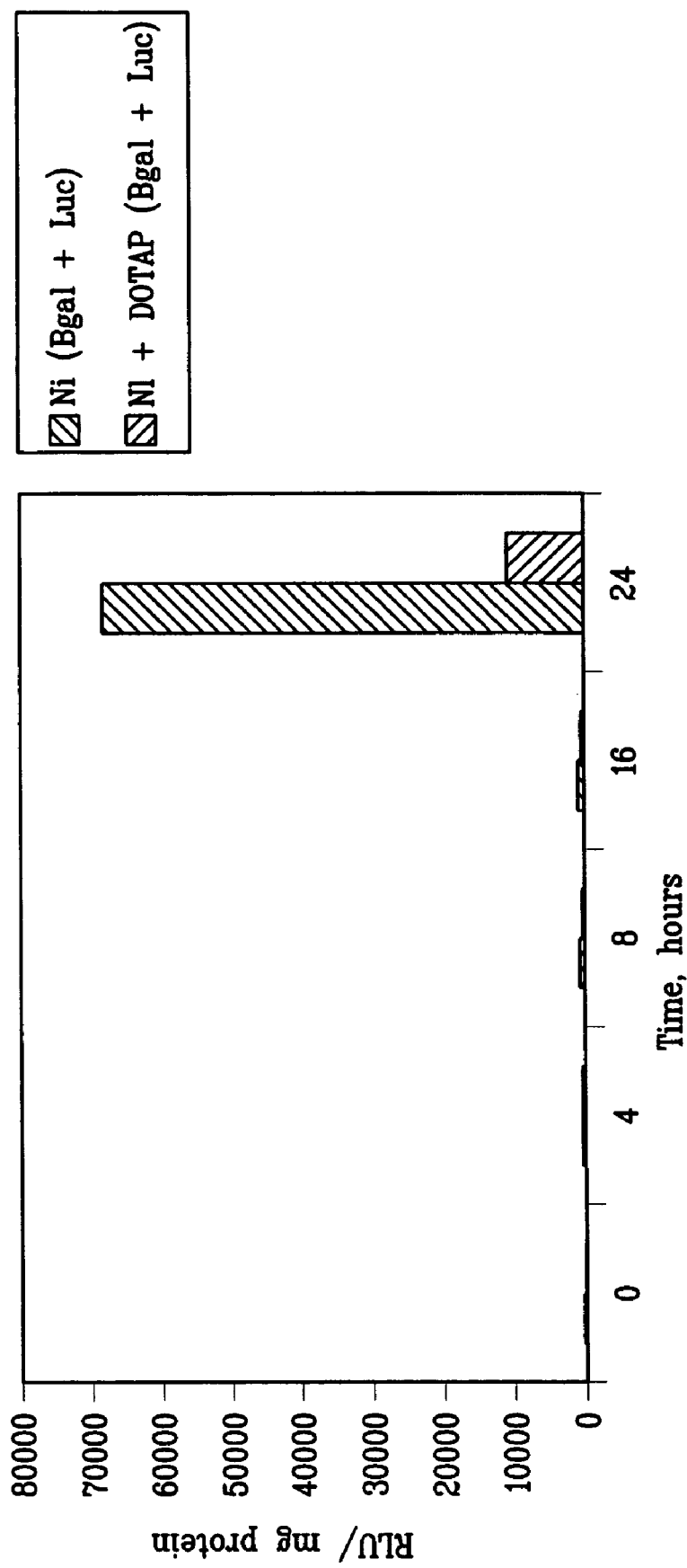
FIG. 4. Histogram depicting the expression of exogenous Luciferase in rats treated with two liposomal formulations. Nonionic (NI) liposomes or NI+DOTAP were formulated to encapsulate 250 µg luciferase DNA and 250 µg β-galactosidase DNA. Luciferase activity was measured at 0, 4, 8, 16 and 24 hours after administration of the liposomal formulations.
Figure 5:
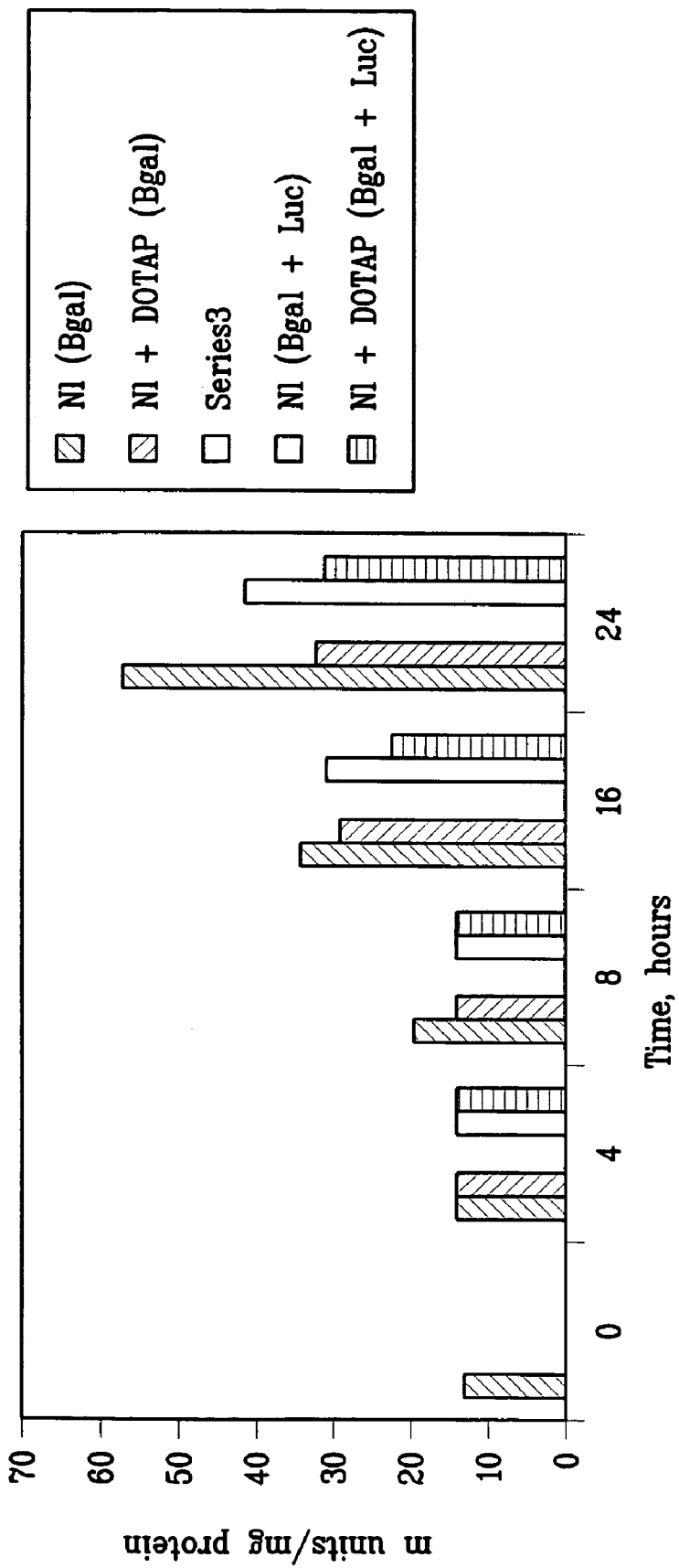
FIG. 5. Histogram depicting the expression of exogenous β-galactosidase activity in rats treated with different liposomal formulations (Exanple 2). Liposomes or other carriers were formulated to encapsulate 250 µg luciferase DNA and 250 µg β-galactosidase DNA. Luciferase activity was measured at 0, 4, 8, 16 and 24 hours after administration of the formulations.

Results:

Comparison of the efficiency of the delivery systems used. The efficiency of the liposomal delivery systems was compared in terms of the expressed product β-galactosidase or Luciferase in the treated skin section by measuring the activity of these two enzymes in the tissue homogenate per mg of the protein extracted. FIG. 4 depicts the expression of exogenous Luciferase in rats treated with the liposomal formulations. Rat pups treated with nonionic (NI) liposomes encapsulating 250 μg luciferase DNA showed maximum expression (95000 RLU/mg protein) after 24 hours of treatment versus NI+DOTAP, and PL formulations. Interestingly, PINC polymer, PEG and the minoxidil carrier system were found to be inefficient in the system described above. A similar trend was observed in the delivery of the β-galactosidase gene and the fluorescent Nile Red. The nonionic liposome formulation was found to be the most efficient delivery system when compared to other delivery systems (FIG. 5). Though the PEG-based minoxidil carrier system alone was found to be an inefficient carrier system, subsequent experiments have demonstrated that a 1:1 mixture of the nonionic liposome formulation and minoxidil carrier are as efficient or more efficient than the nonionic liposome formulation alone in delivering the Nile Red dye to follicle and epidermal cells.

These observations parallel the findings reported by Niemic et al (1997). They have reported that the perifollicular expression of human interleukin-1 receptor antagonist protein following topical application of liposome-plasmid DNA formulations was significantly higher with nonionic liposomes than phospholipid-based liposomes.

Composition of a preferred carrier substance to deliver chemoprotective molecules into the hair follicles. Having identified nonionic liposomes as the most efficient vehicle for transdermal delivery, studies were conducted to deliver various chemoprotective molecules using nonionic liposomes as the carrier molecule, and the efficacy of each of the chemoprotectant molecules in conferring protection against chemotherapy induced alopecia was determined on rat pups treated with Cytoxan.

The nonionic liposome preparations were prepared as described above. Immediately before use an equal volume of the chemoprotective inducer molecules (B-NF, BHA, CG09, Oltipraz, Sulphoraphane and tBHQ) in a suitable solvent was mixed with the liposomes and left at RT for 45 min before being used.

EXAMPLE 4

Microplate Assay for Rapid Screening of Chemoprotective Inducing Agents

The Electrophile Responsive Element (EpRE) has been demonstrated to mediate the induced expression of phase II detoxifying enzymes and oxidative stress proteins which constitutes an important mechanism of cancer chemoprevention. This example describes the development of a rapid, cell-based, functional assay to screen and identify naturally occurring or synthetic chemicals with chemoprotective inducing activity.

Materials and Methods:

Chemicals and Reagents. BHA and TBHQ were purchased from Fluka Chemika (Milwaukee, Wis.). DMSO, β-NF, 3-MC and PDTC were purchased from Sigma Chemical. Oltipraz was obtained from McKesson BioServices (Rockville, Md.). Sulforaphane was purchased from LKA Laboratories, Inc. (St. Paul, Minn.). Synthetic EpRE oligonucleotides were ordered from Integrated DNA Technologies (Coralville, Iowa). The Green Fluorescent Protein expression vector pEGFP was purchased from Clontech (Palo Alto, Calif.). A portion of the DIVERSet™ chemical library, containing 1100 small, hand-synthesized molecules, was purchased from ChemBridge Corporation (San Diego, Calif.).

Cell Culture. The human HepG2 hepatoma cell line was obtained from the American Type Culture Collection (Rockville, Md.) and maintained in DMEM with high glucose containing 10% fetal bovine serum supplemented with 0.1% gentamicin (Life Technologies Inc., Gaithersburg, Md.). The cells were grown at 37° C. in an humidified 5% $CO_2$/95% air atmosphere.

Construction of EpRE-TK-GFP Reporter Genes. Synthetic oligonucleotides containing a 41 bp EpRE motif were annealed and purified, and then with or without a 123 bp Thymidine-Kinase (TK) promoter fragment, were inserted into the multiple cloning site of pEGFP generating EpRE/TK/pEGFP and TK/pEGFP constructs, respectively. By concatamerizing the 41 bp EpRE, multiple EpRE motif copies were also subcloned into pEGFP. The constructed plasmids were purified through Qiagen columns (Qiagen Inc, Santa Clarita, Calif.) and their sequence confirmed by restriction analysis and sequencing which showed that the plasmids contained EpRE and/or TK in the sense orientation.

Transfection Assay. HepG2 cells were seeded at a density of $10^5$ cells/60 mm plate 24 hr prior to transfection. Cells were transfected with 2 μg EpRE/TK/pEGFP or TK/pEGFP plasmids using Lipofectin (Life Technologies, Gaithersburg, Md.) according to the manufacturer's instructions. Clones resistant to 1 mg/ml G418 (Life Technologies, Grand Island, N.Y.) were isolated. After 2-3 weeks, colonies were picked using a microscope and transferred into wells of a 24-well plate for expansion.

Measurement of GFP and Screening Procedure. HepG2 cells ($5\times10^4$) were seeded into wells of a black, clear bottom, tissue culture surface 96-well plate (Becton Dickinson Labware, Franklin Lakes, N.J.) in order to minimize background fluorescence, and after 24 hr then treated with a known chemical or a test compound for an additional 24 hr. The DIVERSet chemical library compounds are packaged at 100 μg/well as a dry film in 96 well plates; after removing the shrinkwrap cover, they were dissolved directly in 100 μl DMSO per well, and part of the compound solution was then further diluted in dilution plates with cell culture medium. The final concentration of test compound in the HepG2 cell wells was around 50 μM. The average molecular weight used for the test compounds was 300. β-NF and tBHQ, as positive controls, were added to wells of the HepG2 plates at 10 μM and 90 μM, respectively. DMSO alone was added to control cultures, and its concentration never exceeded 0.1% in positive control and 1.6% in test compound wells. After a 24 hr exposure to compounds, the medium was removed, 200 μl of PBS containing 100 μg/ml of EtBr was added to stain the HepG2 cells for 20 min at room temperature. The cells were then washed with PBS and 200 μl PBS was added to the wells prior to measuring fluorescence. Measurement of GFP or EtBr fluorescence was performed using a fluorescence microplate reader (Molecular Dynamics, Sunnyvale, Calif.) with excitation/emission at 485 nm/530 nm and 485 nm/612 nm, respectively. Captured data were transferred directly into an Excel computer file for direct data analysis.

Figure 8:
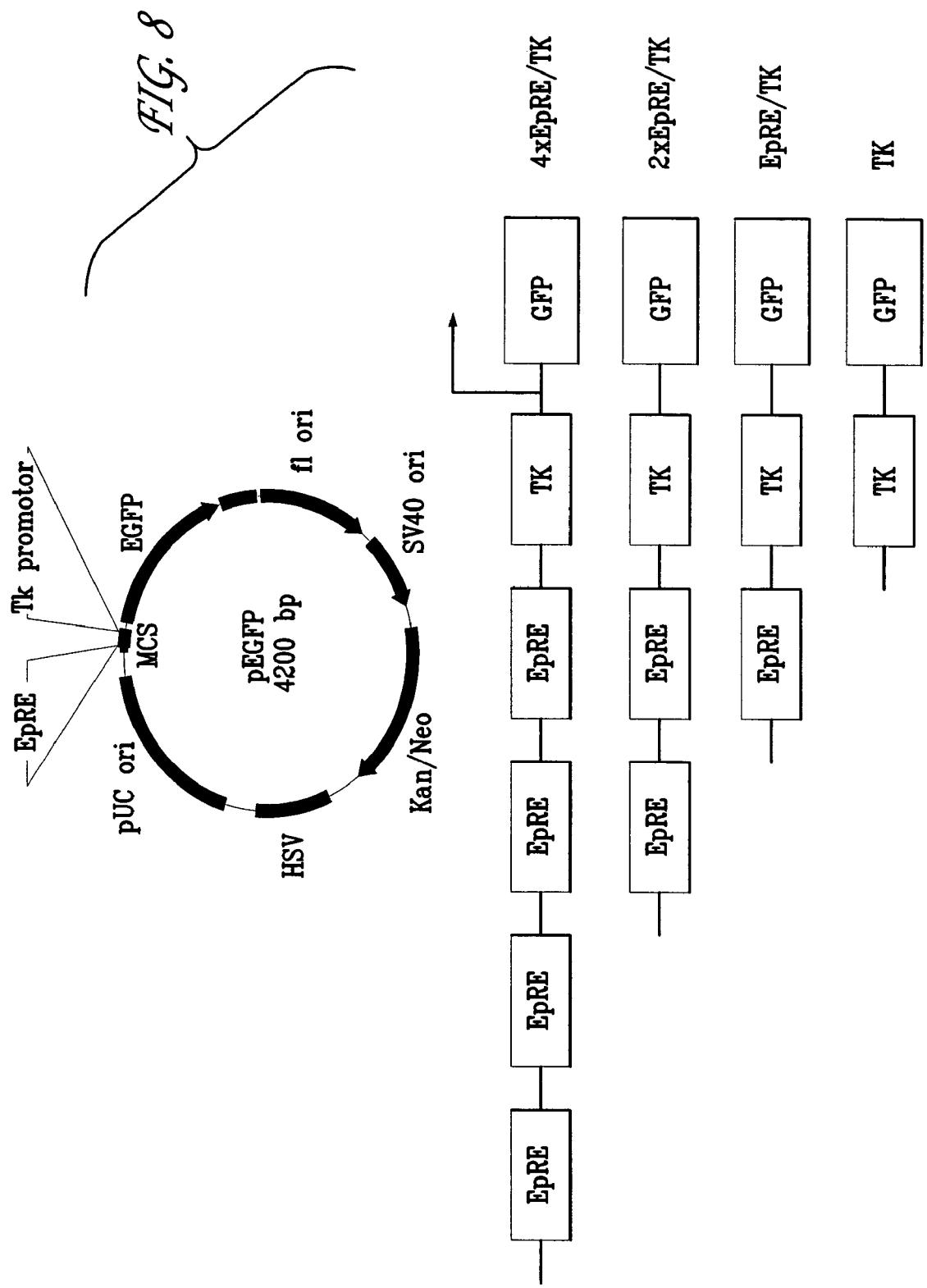
FIG. 8. Construction of the GFP reporter plasmid. Fragments containing single or concatamerized 41 bp EpRE motifs and/or a TK promoter fragment were inserted into a multiple cloning site in the GFP vector.
Figure 9A:
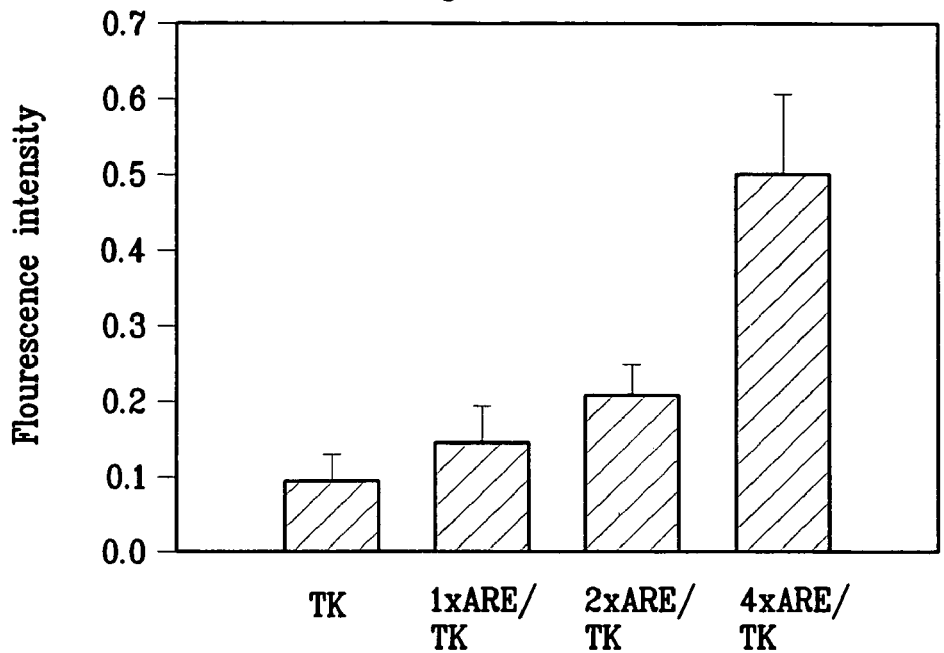
FIG. 9. Basal and induced levels of GFP expression in HepG2 cell clones stably carrying the indicated GFP reporter genes. Cells were treated with 90 mM tBHQ for 24 hr or DMSO (0.1% final concentration) as control. Cells carried the following expression genes: TK-GFP, 1×EpRE/TK-GFP, 2×EpRE/TK-GFP, 4×EpRE/TK-GFP. GFP expression level was determined using a fluorescence plate reader. Values are presented as the mean±S.D.
Figure 9B:
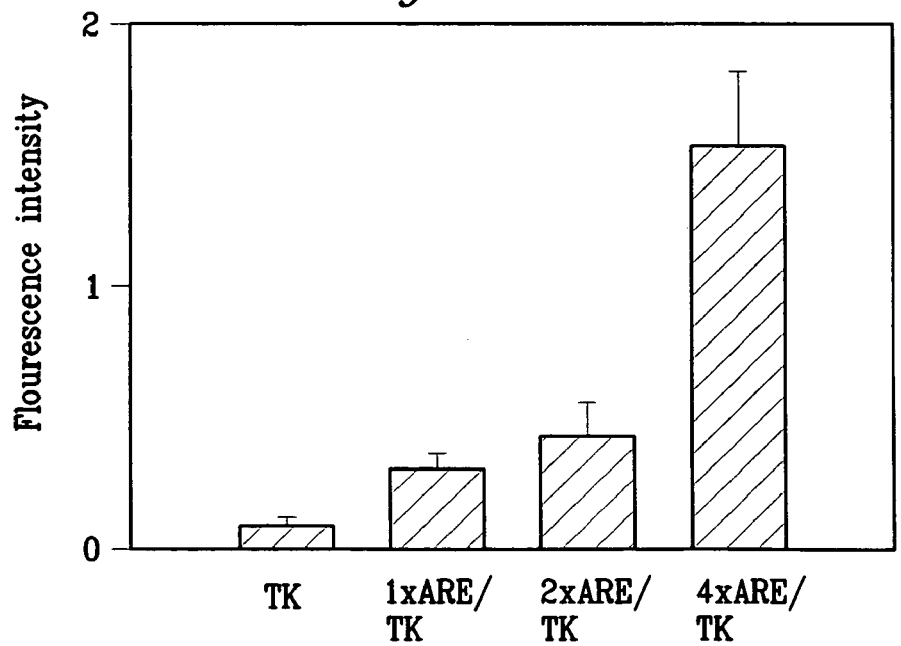

Results:

Construction and Transfection of Reporter Genes. In the reporter gene constructed for this screening system, an EpRE regulatory element and a TK promoter were inserted in front of the GFP reporter gene. In order to enhance the sensitivity of the reporter gene to the stimulus resulting from chemopreventive drug exposure, constructs containing increasing copies of the EpRE element were also made, containing 1×, 2× and 4× copies of the 41 bp EpRE insert (FIG. 8). The fundamental assumption in this screening system is that when cells are exposed to EpRE-activating chemopreventive molecules, the level of intracellular GFP, which reflects the extent to which gene expression is increased, reflects the inducing ability of the test compound. In a final step to creating this test system, transfected HepG2 cell clones showing stable GFP expression, both basal and induced, were isolated and used in the subsequent screening steps.

Basal and Inducible Levels of GFP in HepG2 Cells. The basal and inducible expression levels of GFP in HepG2 cell clones which stably carried reporter genes with different copy numbers of EpRE are shown in FIG. 2. In this experiment, we used tBHQ, one of the primary metabolites of BHA, as the inducer molecule because it has been previously shown to be a potent inducer of the expression of EpRE-dependent genes (Wasserman & Fahl, Proc. Natl. Acad. Sci. USA., 94: 5361-5366, 1997). Metabolic formation of tBHQ is generally considered to be the step responsible for the anti-carcinogenic effects of BHA. There was no discernible difference in the cell proliferation rates between parental HepG2 cells and any of the selected clones that stably expressed the GFP reporter gene. After measuring basal and induced GFP levels in 24 independent clones carrying the 4×EpRE reporter gene, the colony with the highest inducible expression of GFP and the lowest basal level, was used for the subsequent chemical library screening assays.

Figure 10:
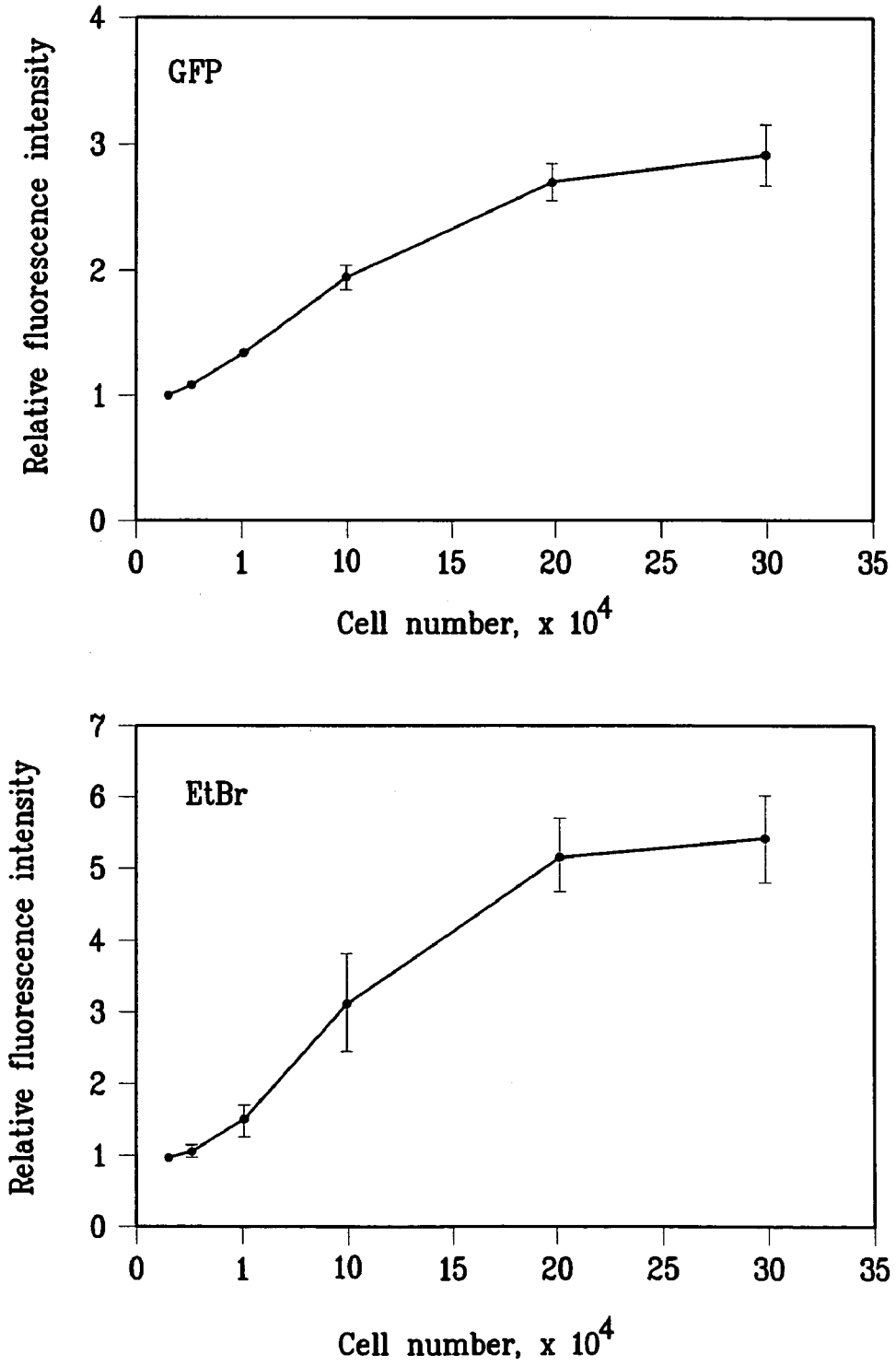
FIG. 10. Correlation between the number of cells plated and DNA content of the well based upon EtBr or GFP fluorescence. Intensity of fluorescence per well was determined as described in Example 4. Values are presented as the means±S.D. for three determinations.

DNA Content as an Internal Standard. Since known chemopreventive molecules and library test compounds could become toxic at certain concentrations and thus suppress cell growth in a given well of a test plate over the two days of drug exposure, it was desirable to standardize the observed GFP level to some indicator of cell number in each microtiter well. Measuring the DNA content of each well was adopted as an internal cell standard. With a primary goal of maintaining screening simplicity, when we considered the overlap of GFP emission wavelength and other available methods used for detecting cell DNA content, we decided to use the DNA staining ability of the intercalating molecule EtBr for the rapid quantitative measurement of DNA content. It was very easy to measure the EtBr signal just by switching the excitation/emission wavelengths in the fluorescence microplate reader. Correlation analysis indicated that there was an excellent correlation between EtBr intensity and cell number (FIG. 10, r=0.9). Therefore, GFP expression levels for each standard and test compound were normalized to the level of EtBr fluorescence found in each well to give a final GFP per cell value.

Figure 11A:
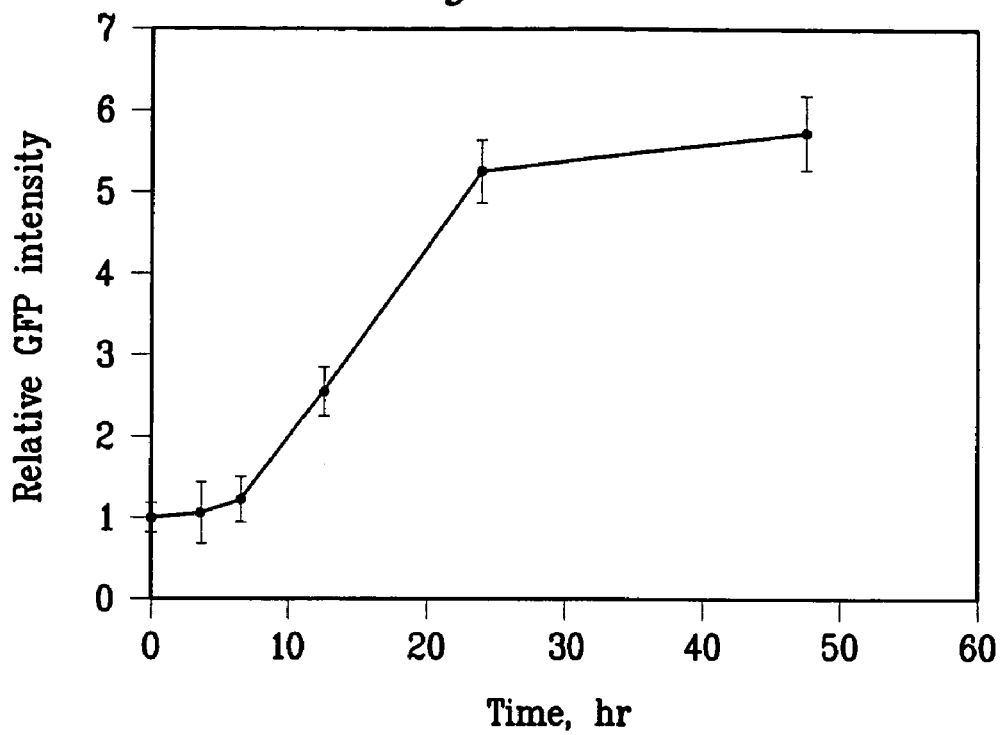
FIG. 11. Time and dose-dependency of GFP expression in tBHQ-treated HepG2 cells. Cells carrying an integrated 4×EpRE/TK reporter construct were treated (A) with 90 µM tBHQ for the indicated times, or (B) with the indicated TBHQ concentration for 24 hr. GFP expression level was determined using a fluorescence plate reader. Values are presented as the means±S.D. for three determinations.
Figure 11B:
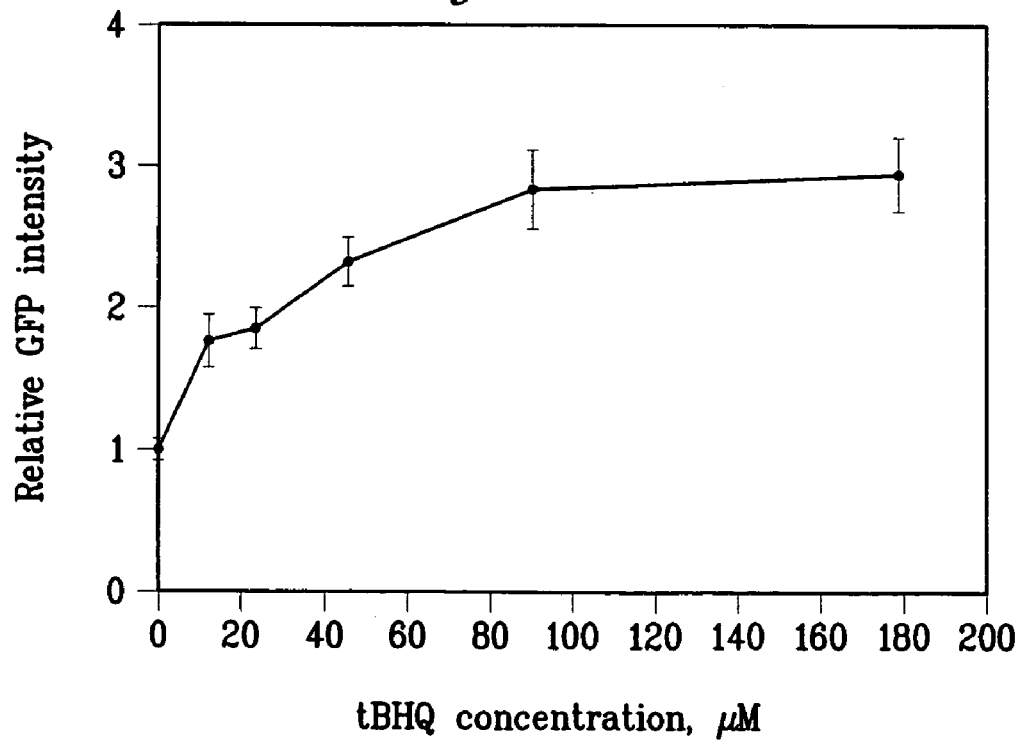
Figure 12:
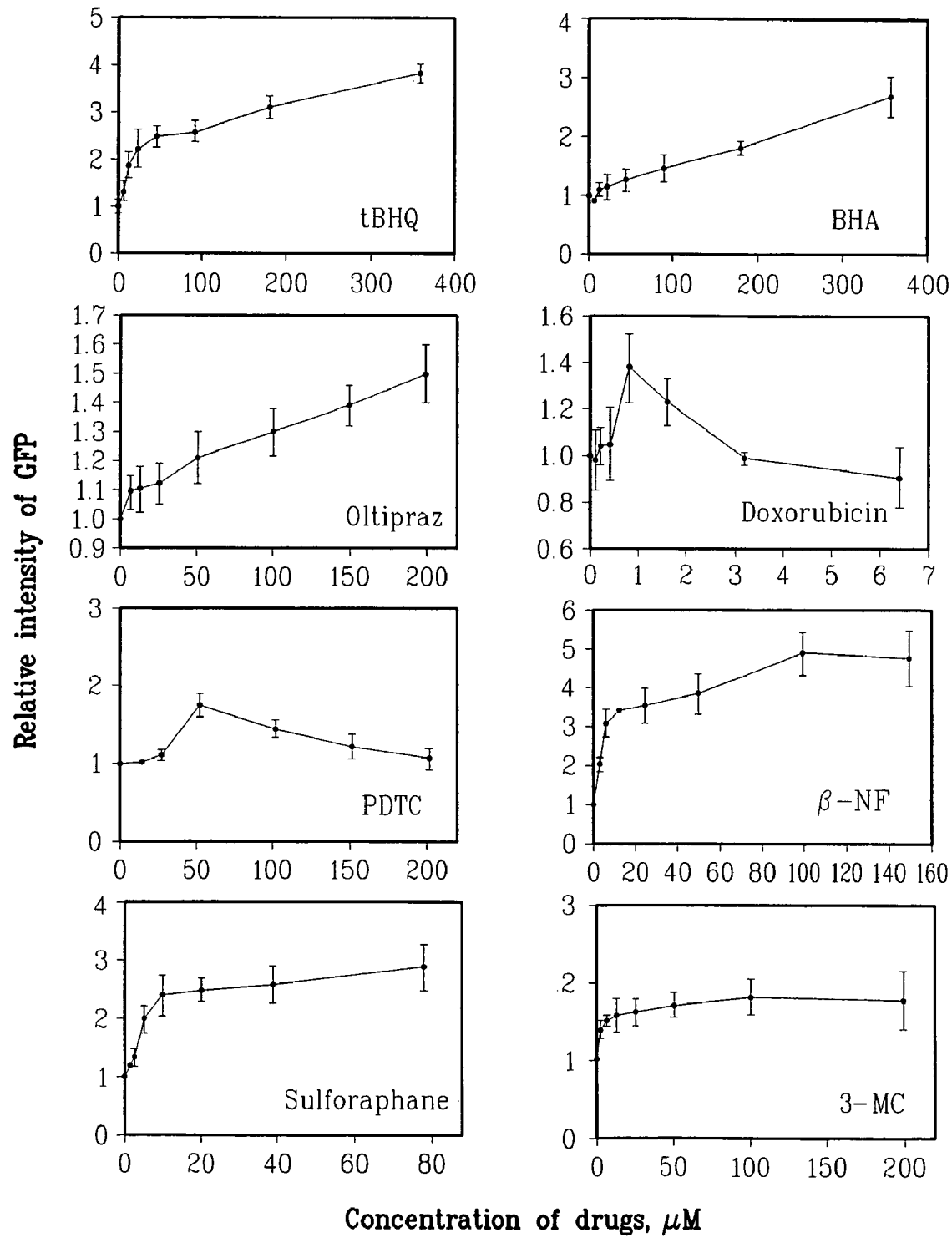
FIG. 12. Dose-dependent induction of GFP expression by known chemopreventive inducer molecules. HepG2 cells were plated in 96-well microtiter plates ($5 \times 10^4$ cells/well) for 24 hr and then treated with the indicated chemicals as described in Materials and Methods. Data are expressed as the means±SD of three parallel cultures. The relative fluorescence intensity ratio was calculated using a value of 1 for the control dish.
Figure 13:
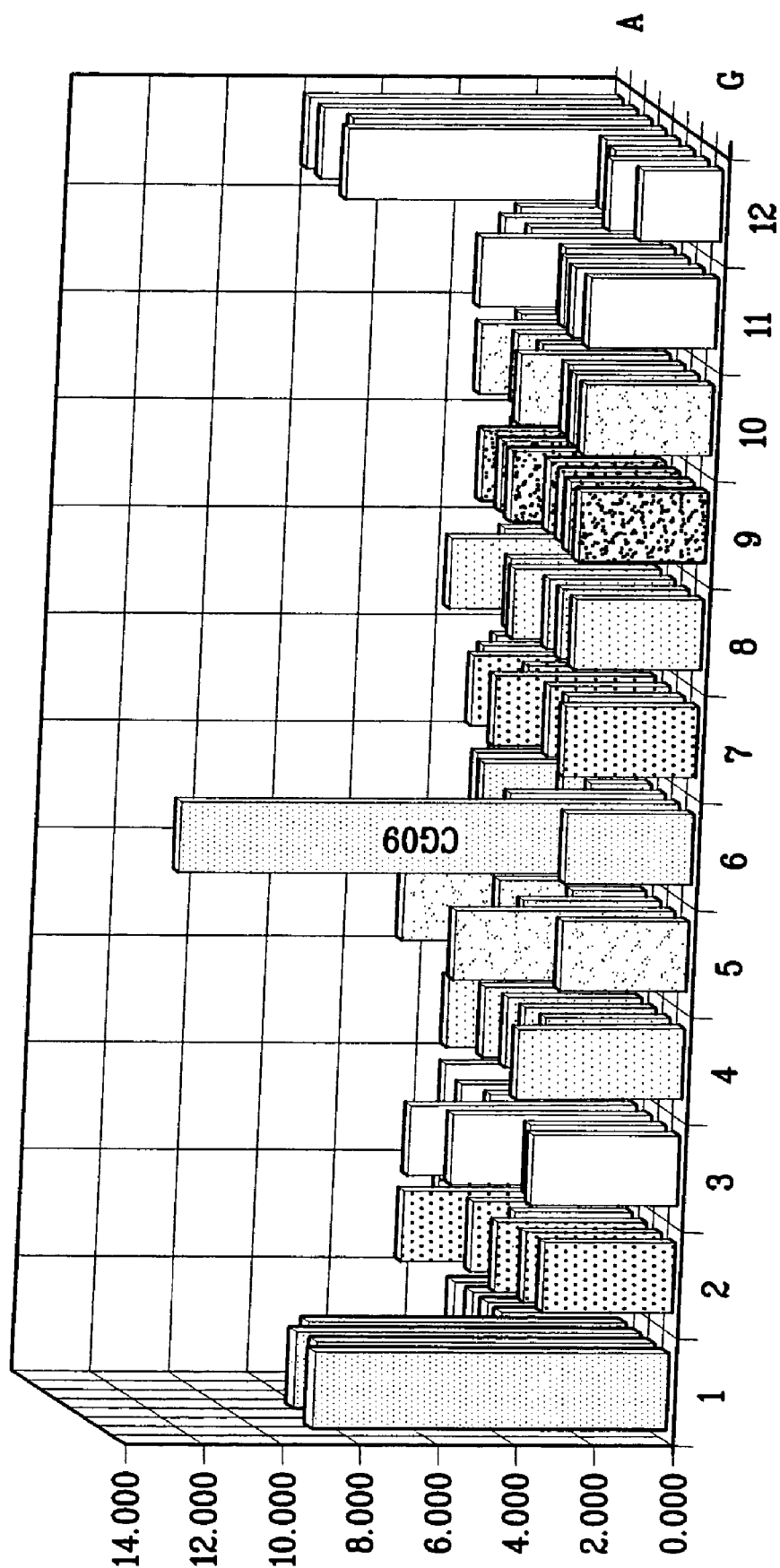
FIG. 13. A typical 3D graph from the screening test which represents the fluorescence data captured from the test plate and analyzed by computer to illustrate the induction level for positive controls (tBHQ, lane 1, and β-NF, lane 12) and each test compound. Compound CG09 is shown in lane 6.

The Expression Level of GFP is Significantly Increased by Known Chemopreventive Molecules. To demonstrate that this cell-based assay could be used to identify new chemopreventive molecules, we tested several of the currently studied chemopreventive molecules to determine how sensitive the screening system would be in detecting them. As a first step, the dose and time dependence of the GFP response following tBHQ treatment were determined (FIG. 11). The level of green fluorescence seen in the HepG2 reporter cells treated for 24 hr with 90 μm tBHQ or 10 μM β-NF are shown in fluorescent images (FIG. 5). Profiles showing the dose-dependent induction of reporter gene expression for eight different molecules are shown in FIG. 12. β-NF is a bifunctional inducer, and it has been widely used in studies of the regulation of both phase I and phase II drug metabolizing genes. BHA, a synthetic phenolic antioxidant, is widely used as a food preservative. Dietary administration of higher doses of BHA has also been shown to confer protection against a variety of chemical carcinogens, this effect attributed to the induction of many phase II detoxifying enzymes in rodents such as GSTs, epoxide hydrolases, and NQO1 (Benson et al., Cancer Res., 38(12): 4486-95, 1978; Benson et al., Proc. Natl. Acad. Sci. USA., 77: 5216-20, 1980). Sulforaphane, isolated from broccoli, is a known inducer of phase II detoxifying enzymes and has been found to inhibit carcinogen-induced mammary tumors in rats (Zhang et al., Proc. Natl. Acad. Sci. USA., 91: 3147-50, 1994; Fahey & Talalay, Food & Chem. Toxicol., 37: 973-9, 1999). Oltipraz, an anti-schistosomal drug molecule which is a substituted 1,2-dithiole-3-thione, is an effective inhibitor of carcinogenesis in many rodent tissues and is an effective inducer of phase II enzymes in vivo, in both humans and rodents (Clapper, Pharmacol. Therapeutics., 78: 17-27, 1998).

Figure 14:
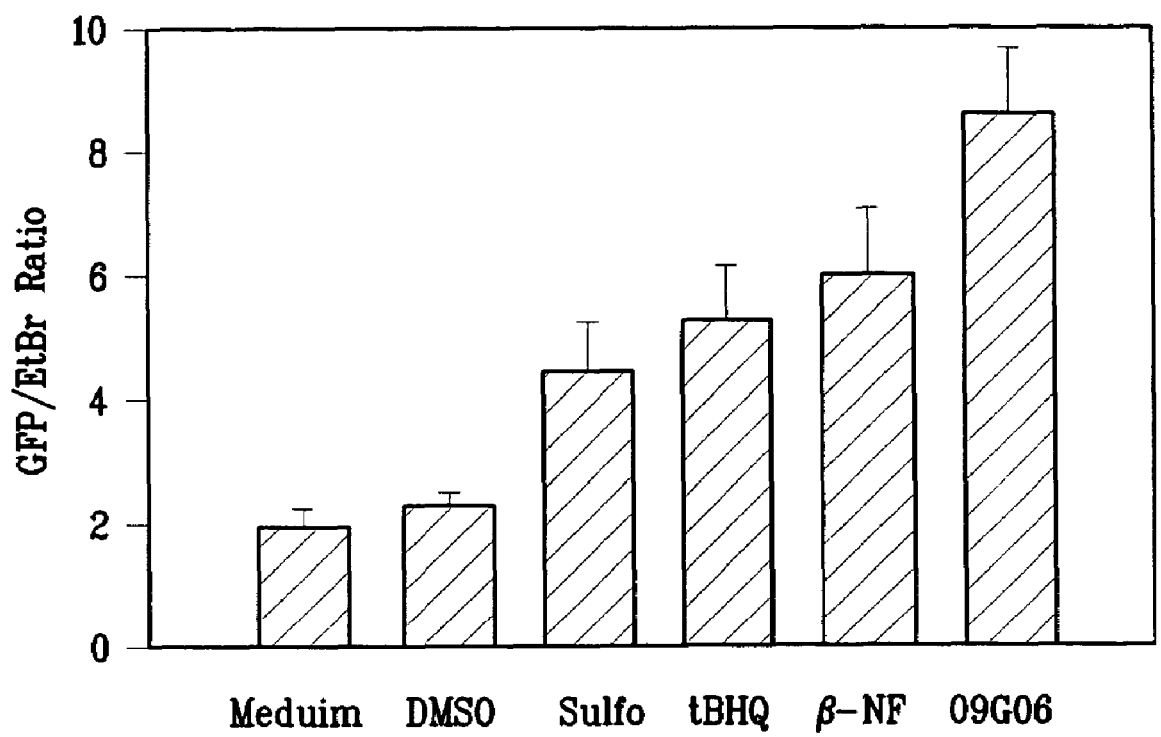
FIG. 14. Level of induced GFP expression from both known inducers and a hit compound (09G06) from the chemical library screening. Data are presented as the mean±SD of three determinations.

Screening of a Chemical Library. In a direct test of the reporter assay's ability to identify chemopreventive, inducing compounds, we screened a chemical library using the described rapid screening assay. FIG. 7 shows a representative 3D graph, processed by computer analysis, that illustrates the induction ability of each test compound and positive and negative control on a representative screening plate. A hit in the screening assay (Compound #09G06), showing induced GFP expression 1.6-fold greater than that seen for the β-NF positive control was identified and is shown in FIG. 14.

EXAMPLE 5

Use of Liposome-Encapsulated Glutathione-S-Transferase to Protect Mammalian Epithelial Cells from the Toxic Effect of Alkylatine Chemotherapeutic Agents Glutathione-S-transferases (GSTs) are present as dimers in cells, with subunit molecular weights in the range of from about 22-30 kDa, and are unable to cross cell membranes. Hence, a mechanism for intracellular delivery of GSTs to target cells is needed to enhance their protective effect during the course of alkylating drug treatment.

Liposomes have been shown to be a suitable non-toxic vehicle for the delivery of drugs, immunogenic proteins, antibodies, DNA, RNA and enzymes, both in vivo and into cultured cells. In this example, we demonstrate the utility of liposomes as an efficient delivery mechanism for introducing large amounts of GSTs into mammalian cells, and the protection conferred by this treatment from the damaging effect of alkylating chemotherapeutic agents.

Described below is the use of cationic, pH-sensitive liposomes to mediate the efficient delivery of GSTs into the cytoplasm of mammalian cells. The studies were conducted using cultured mammalian epithelial cells, an appropriate model system to test the effectiveness of liposome-entrapped detoxifying proteins in conferring protection to cells from drug toxicity.

Materials and Methods:

Preparation of liposomes. Dioleoyl phosphatidylcholine (DOPC), dioleoyl phosphatidylethanolamine (DOPE), 1,2-dioleoxyloxy-3-(trimethylamino)propane (DOTAP), 1,2-dioleoyl-sn-3-succinylglycerol (DOSC), 1,2-dipalmitoyl-sn-3-succinylglycerol (DPSG) were obtained from Avanti Polar Lipids (Birmingham, Ala.). Rat liver glutathione S-transferases (GSTs) were purchased from Sigma Chemical Co. (St. Louis, Mo.).

Lipid films were made by rotoevaporating the lipid in a chloroform solution under argon gas. Large, multilamellar vesicles were prepared by hydrating (vortex mixing) the dry lipid film in 150 mM NaCl, 20 mM HEPES (pH 7.4) containing 0.2-5 mg of purified rat liver GSTs or FITC-conjugated rat liver GSTs (200 ng). The buffer temperature was maintained at a temperature that was approximately ten degrees above the gel-to-liquid-crystalline phase transition temperature of the phospholipid. Lipid concentrations of 50 mg/ml buffer were commonly used. The frozen and thawed multilamellar vesicles were obtained by freezing the large multilamellar vesicles from above in liquid nitrogen and thawing the sample in a water bath at the same temperature used for hydration.

The frozen and thawed large multilamellar vesicles were extruded using a stainless steel extrusion device (Lipex Biomembranes, Vancouver, BC) equipped with a 10 ml water-jacketed barrel attached to circulating water bath which allowed extrusion at elevated temperatures. The vesicles were equilibrated at the appropriate temperature for at least 15 min prior to extrusion. Extrusions were performed through two polycarbonate filters of pore sizes ranging from 100-400 nm in diameter at nitrogen pressures of up to 800 psi. The preparations were subjected to ten repeated cycles through the extruder before usage.

The resulting liposomes were separated from unencapsulated GST by gel-filtration on a Bio-Gel A-15m Gel(Bio-Rad, CA) column (20 cm length×2 cm dia). The fractions containing liposomes were concentrated by spinning for 30 min on a centriprep-500 concentrator (Amicon, Inc., MA).

Cellular uptake of liposomes. Monolayers of COS-7 and AGS cells were grown in Dulbecco's modified Eagle's medium with high glucose (DMEM)/10% (vol/vol) fetal bovine serum in 50-mm culture dishes at 37° C. Prior to liposome exposure, cell monolayers were washed 2 times with DMEM. The cells were then incubated at 37° C. for various lengths of time (0.5-5 hr) in medium containing liposomes. Cell monolayers were washed four times with PBS (phosphate-buffered saline). To quantitatively determine the uptake of FITC-labeled GST in the liposomes by the cells, cell monolayers were thoroughly washed in PBS, scraped off the culture dishes, and lysed in 1 ml of lysis buffer (10 mM Tris-HCL+1% Triton x-100). After centrifuging for 10 min in an Eppendorf centrifuge, the cleared supernatant of the cell extract was retained. The fluorescence associated with this cytosolic extract was then measured using a fluorescence spectrophotometer and converted to units FITC-GST internalized based upon a standard curve obtained with the known amount of FITC-labeled rat liver GST.

Exposure of GST-containing cells to antineoplastic drugs. COS-7 or AGS cells were seeded in 96-well plates and grown overnight in Dulbecco's modified Eagle's medium with high glucose (DMEM-HG) supplemented with 10% (vol/vol) fetal bovine serum (FBS). The following day, cells were washed with serum-free DMEM-HG. Liposomes in DMEM-HG were added to the cell monolayers and incubated 4 hours at 37° C. At the end of the incubation period, monolayers were washed with DMEM-HG supplemented with 10% FBS to remove free liposomes. The antineoplastic drug melphalan was diluted in phenol red-free DMEM-HG containing 10% FBS at the desired concentration and added to the cell monolayers. The multiwell plates were then incubated at 37° C. for 72 hours. Upon completion of the incubation period, the drug-containing medium was removed, and the cells were washed with phenol red-free and FBS-free DMEM-HG to remove residual serum. Cell proliferation was assessed by measuring the conversion of the soluble yellow dye MTT (3-[4,5-Dimethylthiazol-2-y]-2,5-diphenyltetrazolium bromide, Sigma Chemical, St. Louis, Mo.) to an insoluble purple precipitate by living cells. MTT was dissolved at 5 mg/ml in PBS and passed through a 20 µm filter to remove impurities. MTT stock solution was diluted 1:4 in phenol red-free FBS-free DMEM-HG, and 200 µl of this dilution was added to each well of the plate. The plates were incubated 4 hours at 37° C. in the dark, then blotted to remove the MTT solution. The converted dye was solubilized by the addition of 200 µl of acid isopropanol (1.6 ml concentrated HCL in 500 ml isopropanol) to each well of the plate. Absorbance of converted dye was measured at a wavelength of 570 nm with background subtraction at 690 nm.

Results:

Delivery of liposome-encapsulated detoxifying protein to cells. The efficiency of the delivery of detoxifying protein to cells was assessed by quantitating the fluorescence of tagged protein found in the cytosol. When PC liposomes were employed, cells received from about 60-175% more of the fluorescently labeled protein than when no liposomes were employed. Delivery by cationic liposomes (PC+DOTAP) resulted in an increase in fluorescence of from about six to eight fold, relative to delivery by PC liposomes.

Protection of cells by exposure to liposome-encapsulated detoxifying protein. Incubation of COS cells with liposome-encapsulated GST prior to treatment with melphalan, an alkylating antineoplastic agent, conferred protection to the cells. A high MTT absorbance is correlated with a low rate of cell death. Cells not treated with liposome-encapsulated GST had an MTT absorbance that was from about 2 to 25 times lower than that of cells pretreated with liposome-encapsulated GST.

These results demonstrate that pretreatment of epithelial cells with GST-containing liposomes prior to exposure to antineoplasiic agents protects cells against the cytotoxic effects of these agents. In view of the success in protecting cells using GST alone, it is further expected that liposomes comprising both GST and glutathione will be even more effective in protecting cells from the toxic effects of alkylating chemotherapeutic agents, by virtue of providing an additional supply of substrate to increase the activity rate of the GST.

EXAMPLE 6

Modification of Liposomes to Target the Gastrointestinal Epithelium

In the setting of the gut, the incorporation of additional means to allow attachment of the liposomes to the epithelial cell surface would facilitate delivery of liposomal contents to these cells. To increase the specificity of liposomes for lumenal epithelial cells that line the stomach and upper small intestine, the cholera toxin B (CTB) subunit may be covalently attached to the surface of a liposome. Liposomes that have the CTB subunit attached to their surface attach with specificity to cells that express the M1 ganglioside receptor molecule on their surface. Cells that normally express this cell surface molecule include lumenal epithelial cells lining the stomach and upper small intestine. This is the means by which cholera bacterial cells attach to these cells in a natural infection. The B subunit of cholera toxin confers M1 ganglioside receptor binding, but in the absence of the A subunit, confers no toxicity.

Materials and Methods:

Liposome preparation for conjugation to cholera toxin B subunit. Liposomes containing purified rat liver GSTs and trace FITC-conjugated rat liver GST were prepared and purified by the standard extrusion protocol described in Example 1, using the following mixture of lipids: phosphatidylcholine (PC): phosphatidylethnolamine (PE): 1,2-Dioleoyl-sn-glycero-3 phosphaethanolamine-N-[4]-(p-maleimidophenyl)butyrate (N-MBP-PE), 70:20:10 Mol %.

Chemical modification of cholera toxin B subunit (CTB) for cross-linking to liposomes. A primary amine reactive reagent was used to add thiol groups to the lysine residues of CTB. The thiol groups were necessary for reaction with the maleimide group on the N-MPB-PE-containing liposomes. To achieve this, CTB (100 μg) was dissolved in HEPES-saline buffer and incubated with N-succinimidyl 3-(2-pyridyldithio)propionate (SPDF) at a 1:100 molar ratio in the dark at room temperature for one hour. The reaction was quenched by adding 10 μl of 20 mM L-lysine in 20 mM Tris-HCl (pH 6.8) and the reaction products were then reduced by adding 5 μl of 7.7 mg/ml dithiothreitol in water. Unreacted substances were removed by passing the reaction mixture through a size exclusion Sephadex G25 spin column. The concentration of the activated CTB in the excluded fraction was measured by Coomassie protein assay reagent (Pierce Biochemical, Rockford, Ill.).

Cross-linking of activated CTB to liposomes. Conjugation of activated CTB to liposomes containing GST and trace FITC-conjugated GST was carried out by incubating the reduced CTB (50 μg) with a suspension of 1 mL N-MBP-PE-bearing liposomes at 5° C. overnight. The coupling reaction was stopped by adding 10 μl of L-cysteine buffer (20 mM L-cysteine in 20 mM Tris-HCL buffer, pH7.2). The CTB-conjugated liposomes were purified from unconjugated CTB on a size exclusion gel filtration column (Biogel A-15m gel, Bio-Rad Laboratories, CA; 15 cm long×2 cm diameter) pre-equilibrated with HEPES-saline buffer. The liposomes were eluted in 0.5 ml fractions and the liposome content of each fraction was determined by fluorescence and GST activity. Liposome-containing fractions were pooled (fractions #5-9) and concentrated to 1 ml by centrifugation at 1000×g for 30 min using a Centriprep 500 concentrator (Amicon Inc., Beverly Mass.).

Cellular uptake of CTB liposomes. Cells ($6\times10^6$ HuTu or COS cells) were seeded into 60 mm dishes and grown overnight in DMEM with high glucose (DMEM w/HG) supplemented with 10% fetal calf serum (FCS) in a humidified atmosphere of 10% $CO_2$. The monolayers were then washed three times with 5 ml of DMEM w/HG+HEPES saline (50 mM HEPES+50 mM NaCl, ph 7.5). To test the ability of the CTB-conjugated liposomes to bind specifically to cells bearing the GM1 ganglioside receptor, some dishes were pre-treated for 10 min with a commercially-available sample of GM1 ganglioside receptor (20 μg). A 100 μl sample of CTB-conjugated liposomes (containing 5000 fluorescence units of FITC-conjugated GST) was added to each monolayer with 5 ml DMEM w/HG+HEPES saline buffer, and incubated for 4 hours at 37° C. The cell monolayers were then washed 4 times with 5 ml PBS to remove unbound CTB-conjugated liposomes. The amount of CTB-conjugated liposomes bound/internalized to the cells was quantified by first scraping the cells from the culture dish, resuspending in 0.3 ml PBS and sonicating for 30 seconds. A 20 μl aliquot of each cell lysate was added to 2 ml of PBS, and the amount of cell-associated fluorescence was measured (excitation/emission maxima 494/520 nm) in a fluorometer. The concentration of protein in the cell lysate was determined using the Coomassie protein estimation kit.

Results:

The use of liposomes having the CTB subunit attached to the liposome surface resulted in enhanced delivery of labeled protein to gastrointestinal carcinoma cells (HuTu cells), but not to kidney tubule epithelial cells. (COS cells). The increased efficiency conferred by the CTB subunit was quenched in the presence of an excess of free M1 Ganglioside receptor. These results demonstrate that liposomes are effectively modified to target cells of the gastrointestinal epithelium by incorporation of the CTB subunit onto their surfaces.

The present invention is not limited to the embodiments described and exemplified above, but is capable of variation and modification without departure from the scope of the appended claims.

We claim:

1. A method for reducing or preventing hair loss in a patient caused by administration of a chemotherapeutic agent comprising cyclophosphamide, the method comprising administering to the patient's cells lining hair follicles an effective amount and for an effective duration a pharmaceutical preparation comprising a compound according to the structure and one or more nonionic liposomes, wherein the chemoprotective inducing agent induces or increases production of glutathione-S-transferase Ya.

* * * * *